(12) United States Patent
Fadel et al.

(10) Patent No.: US 7,517,840 B2
(45) Date of Patent: *Apr. 14, 2009

(54) OPTIMIZED PERFUMERY FOR RINSE-OFF PRODUCTS

(75) Inventors: Addi Fadel, Shelton, CT (US); Richard Turk, Plymouth, MA (US); Grant Mudge, West Redding, CT (US); Jill Mattila, Greensboro, NC (US); Veronica Goberdhan, Fairfield, CT (US)

(73) Assignee: Givaudan Fragrances Corporation, Mount Olive, NJ (US)

( * ) Notice: Subject to any disclaimer, the term of this patent is extended or adjusted under 35 U.S.C. 154(b) by 385 days.

This patent is subject to a terminal disclaimer.

(21) Appl. No.: 11/400,323

(22) Filed: Apr. 7, 2006

(65) Prior Publication Data

US 2007/0042934 A1    Feb. 22, 2007

Related U.S. Application Data

(60) Provisional application No. 60/669,120, filed on Apr. 7, 2005.

(51) Int. Cl.
   *C11D 3/50*    (2006.01)
(52) U.S. Cl. .......................................... 510/101; 512/1
(58) Field of Classification Search ..................... 512/1; 510/101
   See application file for complete search history.

(56) References Cited

U.S. PATENT DOCUMENTS

| | | | |
|---|---|---|---|
| 5,703,250 A | 12/1997 | Bajgrowicz | 549/369 |
| 6,143,707 A | 11/2000 | Trinh et al. | 510/220 |
| 6,455,086 B1 | 9/2002 | Trinh et al. | 426/321 |
| 6,601,789 B1 | 8/2003 | Bajadali et al. | 241/301 |
| 6,858,574 B2 | 2/2005 | Yang et al. | 512/1 |
| 2002/0055452 A1 | 5/2002 | McGee et al. | 512/2 |
| 2003/0022805 A1 | 1/2003 | Clare | 510/220 |
| 2003/0166498 A1 | 9/2003 | Yang et al. | 512/1 |
| 2004/0138078 A1 | 7/2004 | Clare et al. | 510/220 |
| 2005/0096252 A1 | 5/2005 | Dubois et al. | 512/1 |
| 2006/0003031 A1* | 1/2006 | Fadel et al. | 424/725 |
| 2006/0207037 A1 | 9/2006 | Fadel et al. | 8/406 |
| 2007/0042934 A1* | 2/2007 | Fadel et al. | 512/1 |
| 2007/0099804 A1* | 5/2007 | Fadel et al. | 510/101 |
| 2008/0176781 A1* | 7/2008 | Fadel et al. | 510/106 |

FOREIGN PATENT DOCUMENTS

| | | |
|---|---|---|
| EP | 1 146 057 | 10/2001 |
| EP | 1 249 446 A2 | 10/2002 |
| EP | 0 888 440 B1 | 1/2003 |
| EP | 1 297 854 A1 | 4/2003 |
| EP | 1 318 190 A1 | 6/2003 |
| EP | 1 340 741 A1 | 9/2003 |
| WO | WO 97/34987 | 9/1997 |
| WO | WO 02/064722 A2 | 8/2002 |

OTHER PUBLICATIONS

University of Georgia Engineering Dept., *Conserving Water at Home*, Circular 819-1, Apr. 1991, published at http://www.engr.uga.edu/service/extension/publications/c819-1.html.

* cited by examiner

*Primary Examiner*—Mark Eashoo
*Assistant Examiner*—M. Reza Asdjodi
(74) *Attorney, Agent, or Firm*—Morgan Lewis & Bockius LLP

(57) ABSTRACT

Perfume compositions and method of formulating perfume compositions designed for use in rinse-off or high dilution systems provide a sustained linear release and/or a delayed release, with the odorants selected according to their mass transfer values, odor detection thresholds and/or calculated odor indices.

20 Claims, 6 Drawing Sheets

OPTIMIZED PERFUMERY FOR RINSE-OFF PRODUCTS

CROSS-REFERENCE TO RELATED APPLICATIONS

Applicants claim priority benefits under 35 U.S.C. §119(e) of U.S. Provisional Patent Application Ser. No. 60/669,120 filed Apr. 7, 2005.

FIELD OF THE INVENTION

The present invention relates to perfume systems. More particularly, the present invention relates to the optimization of perfumes used in high water dilution conditions and/or rinse-off applications.

BACKGROUND OF THE INVENTION

Fragrances are an important part of cosmetic compositions since their primary role is to create an agreeable sensory experience for their consumer, in addition to providing malodor coverage or other more functional roles.

Perfumes are composed of odorants with a wide range of chemical properties including molecular weights, vapor pressures and diffusivities as well as different polarities and chemical functionalities. Using these different properties, one can create different hedonic profiles describing the fragrance.

Fragrance materials are generally small molecular weight substances with a vapor pressure that allows their molecules to evaporate, become airborne, and eventually reach the olfactory organ of a living entity.

There are a variety of different fragrance materials with different functional groups and molecular weights, both of which affect their vapor pressures and hence the ease with which they can be sensed.

Odorants used in perfumery offer a wide array of polarity ranging from the somewhat water miscible to the water immiscible chemical compounds. Perfumery in the various wash-off applications spanning from cosmetic to industrial and household have different functionalities and must be engineered to fulfill certain needs and objectives. Perfumes' effect and quality during use plays a big role in the consumer's purchase intent as well and the desire of the consumer to purchase the product again.

Prior art pertaining to perfumery for water based rinse-off applications deals largely with general physical properties of odorants such as boiling point and clogP values. U.S. Pat. No. 6,143,707 discloses automatic dishwashing detergent with what is defined as blooming fragrance compositions by the authors. These perfumes contain so-called "blooming perfume ingredients," and optional "delayed blooming" ingredients as well as "non-blooming ingredients." "Blooming" odorants were chosen based on their clogP and boiling point values. The logP value of an odorant is defined as the ratio between its equilibrium concentration in octanol and in water. The logP value of many of the fragrance materials have been reported and are available in databases such as the Pomona92 database, the Daylight Chemical Information Systems, Inc, Irvine, Calif. The logP can also be very conveniently calculated using the fragment approach of Hansch and Leo. See A. Leo, Comprehensive Medicinal Chemistry, Vol. 4, C. Hansch et al. p 295, Pergamon press, 1990. These logP values are referred to as clogP values. Odorants thought to result in bloom in water dilutions are thought to have clogP of at least 3.0 and boiling points of less than 260° C.

The same rationale for dishwashing liquids with blooming perfumes was also filed in U.S. Patent Application No. 2004/0138078. EP Patent No. 0888440B1 relates to a glass cleaning composition containing "blooming perfumes" based on criteria mentioned above. U.S. Pat. No. 6,601,789 discloses toilet bowl cleaning compositions also containing "blooming perfumes" made of odorants chosen based on their clogP values of at least 3.0 and boiling points of less that 260° C. Odorants with delayed bloom are thought to have a clogP of less than 3.0 and boiling point values less than 250° C.

SUMMARY OF THE INVENTION

A method of formulating a perfume composition for rinse-off or high dilution systems, comprising calculating water release ($\Omega$) values for a group of odorants, selecting at least two odorants based on these values and their elution from specific water release groups, and placing the odorants in the perfume composition for a rinse-off or high dilution system to provide a delayed release of perfume therefrom, is provided.

A method of formulating a perfume composition for rinse-off or high dilution systems, comprising calculating water release ($\Omega$ values for a group of odorants, selecting at least three odorants having different values and eluting in different release groups, and placing the odorants in the perfume composition for a rinse-off or high dilution system to provide a sustained linear release of perfume therefrom, is provided.

DETAILED DESCRIPTION OF THE INVENTION

Figure 1:
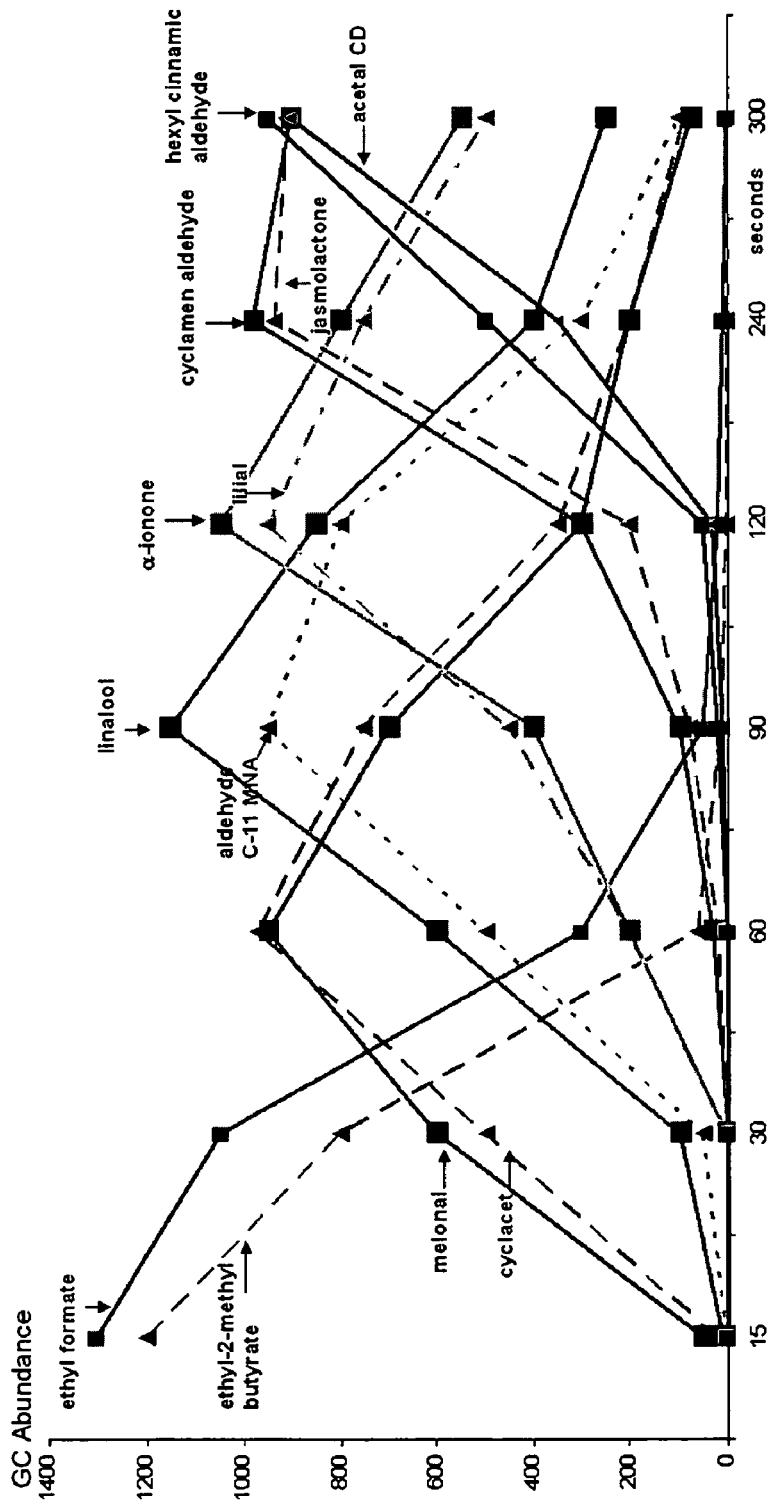
FIG. 1 is a graph showing odorants' residence time in headspace according to their $\Gamma$ values.

This invention relates to the optimization of perfume or fragrance diffusion from the product of high water dilution, based on odorants' calculated mass transfer properties.

This invention relates to the design and engineering of perfume or fragrance by selecting odorants based upon mass transfer properties and transport properties in water-based partitions, water vapor and air, aiming to give the released perception of a single hedonic note in heavy water dilutions, which is termed "linear release."

Perfumes engineered for rinse-off applications according to the methods described in the herein invention will result in a sustained "linear" release of a particular olfactive note, or a hedonic note lasting throughout the entire rinse-off experience.

Perfumes designed for sustained "linear release" are based on odorants' water release $\Omega$, derived pseudo-acceleration $\Gamma$, odor detection threshold and/or odor index values in water and/or air as defined herein. In order to achieve a linearly released fragrance note during rinse-off, the odorants used as part of the sustained linearly released fragrance note must contain at least three different odorants, which are part of the engineered sustained and linearly released perfume note. These three odorants must elute in at least three different "water release groups" based on odorants Ω values and as defined in the herein invention.

Additionally, at least one odorant having a water release value of 0.007 or higher (units of $$\left(\frac{\text{Force}}{\text{Area}}\right) \times \frac{1}{\text{time}}$$

as defined in this invention) or in other words, belonging to either Water release groups/ranges 1, 2 or 3 may be selected for use as part of the sustained linearly released fragrance note.

Additionally, at least one odorant having a derived pseudo-acceleration values Γ between 100 and 1000 (cm/sec$^2$), corresponding to sustained release value in water dilutions, may be selected for use as part of the sustained linearly released fragrance note.

Additionally, at least one odorant having an odor detection threshold value in water and/or an odor index determined in water of 50 parts per billion or less may be selected for use as part of the sustained linearly released fragrance note.

Additionally, at least one odorant having an odor detection threshold in air and/or odor index determined in air of 0.025 mg/m$^3$ or less may be selected for use as part of the sustained linearly released fragrance note.

Additionally, this invention relates to the design and engineering of perfume or fragrance causing a change in the overall character of the released perfume during rinse-off, which is termed "delayed release" of a perfume character or note. This delayed release is achieved without the use of encapsulation methods or other means of delivery presently known in the art, and instead selects odorants based upon mass transfer properties and physical thermodynamic properties in water, water/air and air partitions. This change in the perfume note can be drastic and/or progressive based on mass transfer values of the chosen odorants.

Perfumes designed for "delayed release" of a fragrance note are constructed based on odorants' predicted elution behavior out of large water dilutions, simulating rinse-off conditions. These odorants release into headspace during rinse-off are predicted based on their water release Ω and derived pseudo-acceleration Γ values. Their perceived intensity is in turn gauged by their odor detection threshold and/or odor index values in water and/or air as defined by the authors. The designed fragrance key engineered for delayed release in rinse-off conditions must have at least two different odorants, preferably at least three different odorants, contributing to the delayed odor.

The odorants contributing to the delayed odor have water release values lower than 0.007 (units of $$\left(\frac{\text{Force}}{\text{Area}}\right) \times \frac{1}{\text{time}}$$

as defined in this invention), and therefore elute in rinse-off conditions as part of Water Release Groups 4 and/or 5 and/or 6 and preferably as part of Water Release Groups 5 and/or 6 (or in other words, Ω less than 0.0005)

Additionally, at least one odorant having a derived pseudo-acceleration values Γ between 100 and 1000 (cm/sec$^2$), corresponding to sustained release in water dilutions, may be selected to contribute to the delayed release perfume character.

Additionally, at least one odorant having an odor detection threshold value in water and/or an odor index determined in water of 50 parts per billion or less may be selected for use as part of the delayed release fragrance.

Additionally, at least one odorant having an odor detection threshold in air and/or odor index determined in air of 0.025 mg/m$^3$ or less may be selected for use as part of the sustained delayed release fragrance note.

The perfumes designed according to methods described herein give the consumer the perception of a burst or slow release of a certain smell, olfactive note and/or odor based on their constituent odorants' mass transfer values and physical thermodynamic properties in various partitions described herein.

In water-based systems, choosing fragrance molecules or odorants (to be incorporated into a perfume) based on specific mass-transfer values for release out of a matrix optimizes the perfume's intensity and perceived hedonic quality. These values are calculated according to these odorants' physico-chemical properties based on principles of mass transfer.

In addition, by constructing the perfume according to predicted and calculated water release values, one can engineer the delayed and/or superior sustained linear release of a certain olfactive note during application of the product containing the said-perfume.

According to the present invention, a perfume composition is optimized for various cosmetic, household and industrial applications in water-bases systems, or in presence of water, by selecting odorants based upon their water release values (Ω) pseudo-acceleration values (Γ), and their estimated odor impact values as calculated within the defined water release groups, as described herein.

The general physical properties of perfume odorants as currently known in the art (e.g., U.S. Pat. No. 6,143,707, U.S. Patent Application Pub. No. 2004/0138078, EP Patent No. 0888440B1, and U.S. Pat. No. 6,601,789) do not provide a complete picture when creating perfumes for rinse-off systems. In fact, there disclosure can even be counter to empirical findings. For example, odorants such as ethyl formate, ethyl acetoacetate, ethyl acetate, diethyl malonate, fructone, ethyl propionate, toluic aldehyde, leaf aldehyde, trans-2-hexenal, trans-2-hexenol, cis-3-hexenol, prenyl acetate, ethyl butyrate, hexanal, butyl acetate, 2-phenylpropanal, cis-4-heptenal, cis-3-hexenyl formate, propyl butyrate, amyl acetate, ethyl-2-methylbutyrate, ethyl amyl ketone, hexyl formate, 3-phenyl butanal, cis-3-hexenyl methyl carbonate, methyl phenyl carbinyl acetate, methyl hexyl ether, methyl cyclopentylidene acetate, 1-octen-3-ol, cis-3-hexenyl acetate, amyl vinyl carbinol, 2,4-dimethyl-3-cyclohexen-1-carbaldehyde, ethyl 2-methylpentanoate, 1,3,3-trimethyl-2-oxabicyclo[2.2.2]octane, 3,7-dimethyl-7-methoxyoctan-2-ol etc. are considered to have superior release properties in heavy water dilutions. The above mentioned odorants are considered "delayed release" odorants according to the above-listed references, which is counter to both empirical and experimental observations when used in wash-off products.

Furthermore, a direct relationship between the quantity of an odorant in a perfume and its ability to be released from the water partition under heavy water dilution is generally observed by perfumers skilled in the art. The opposite can also hold true when using very small amounts of an odorant in a perfume. A mathematical relationship relating quantity of odorants in perfumes to their mass transfer properties needs to be established in order to predict the order of elution of perfume constituents when exposed to heavy water dilutions. For example, thiogeraniol (clogP 4.88, boiling point 250° C.) can have very delayed water release properties when used in parts per trillion in a perfume although considered a "blooming" material based on its physical properties. Once this mathematical relationship is established, one can design and further improve water release hedonic perception of perfume materials. The result is the optimization and applied perfumery for wash off applications.

U.S. Pat. No. 6,858,574 relates odorants release properties in heavy water dilution to a relationship with components of the formulation in which the perfume is delivered, more notably, the surfactant system. The so-called perfume burst index (PBI) is defined by:

$$PBI = \frac{\phi - 1.4/CMC}{K}$$

where $\phi$ is water/oil partition coefficient (an equivalent to clogP mentioned above), K is the volatility constant of perfumes in air (in direct relationship to boiling point values) and CMC is the critical micellization concentration of the surfactant systems (wt/wt). A burst release in water dilutions is thought to happen when there is at least 20% increase of the odorant in headspace. Examples provided by the author are done in dilutions not exceeding 60 and mostly between 0 and 30. Yet, consumer usage of formulations in wash off conditions, especially in applications such as body wash, conditions, shampoos, surface cleaners, etc. . . . the conditions far exceed the dilution values used by the authors for their calculations. For example, a typical usage of water during a shower exceeds 25 gallons of water and can reach 50 gallons of water when considering a typical household shower pressure dispensing 5-10 gallons a minute (See "Conserving Water at Home," University of Georgia, Engineering Dept., available at http://www.engr.uga.edu/service/extension/publications/c819-1.html). Values for water dilutions in a typical household, cosmetic, industrial wash-off application therefore far exceeds the dilution values used by the author in the above mentioned patent. One can therefore argue that the release partitions under these extreme conditions become essentially water, water-air and air with surfactants' contributions very minimal, almost non existent.

In the present invention, mass transfer properties of odorants in water as well as their odor detection thresholds determined either experimentally or theoretically are used to design fragrances optimized for water release. The abovementioned physico-chemical properties of odorants are utilized in methods described in this invention to control and engineer superior olfactive perception of these perfumes, whether sustained linear release and/or delayed release as descried herein, during their use and release in the presence of water with resulting effects required by the rinse-off applications in which they are delivered.

According to the present invention, a perfume composition is optimized for various cosmetic, personal, household and industrial applications in water systems and/or in presence of water and/or in high dilution systems. The odorants selected based upon their designated water release value, as defined in the present invention, to perfumes may comprise at least about 30%, and preferably at least about 40% of the total fragrance, depending on the applications considered and described herein.

Perfume compositions according to the present invention may be utilized in any water-based system, including but not limited to cosmetic, personal, household and industrial soaps, detergents and other products generally, including those for kitchen use, such as kitchen cleaner, dishwashing liquid and dishwasher detergent, for laundry use, such as laundry detergent, liquid fabric softener and stain treatment, and for personal use such as face, hand and soap body soap, wash, cleanser, scrub, gel, lotion, rinse-off moisturizer and the like.

These products also may contain natural or synthetic extracts providing an added benefit agent to the user during the application. For example, many body wash shampoo and conditioners will include some benefit agent or conditioning agent, usually in the form of a natural extract as a benefit agent. Based on methods described in this invention, one can create a time delayed hedonic release (also referred to by the authors as "delayed release") that goes along with an added benefit agent to give the consumer the impression of delivered added benefit included in a formulation. The methods included in this herein invention can also serve to engineer a continuous sustained release of a particular hedonic note throughout the time of the rinse-off (also referred to by the authors as "linear release"), emphasizing the benefit agent throughout the entire rinse-off experience and further accentuating the sensory perception of the consumer using the product.

In the present invention, mass transfer properties of odorants in water as well as their odor detection thresholds determined either experimentally or theoretically are used to design fragrances optimized for water release. The abovementioned physico-chemical properties of odorants are utilized in methods described in this invention to control and engineer the consumer gradual and time-related olfactive perception of these perfumes during their use and release in the presence of water.

According to the present invention, a perfume composition is optimized for various cosmetic, household and industrial applications in water systems and/or in presence of water using perfume odorants' water release values $\Omega$ as calculated in the herein invention, calculated pseudo-acceleration values $\Gamma$ and their estimated odor impact values within the defined water release groups.

In addition, the perfumes designed according to methods described in this invention give the consumer the perception of a burst or slow release of a certain smell, olfactive note and/or odor based on their constituting odorants mass transfer values and physical thermodynamic properties in various partitions mentioned herein.

Water Release, $\Omega$

Water release value ($\Omega$) is defined by the authors as being the product of quantity of an odorant in a perfume totaling 100 parts, flux ($\Phi$), pseudo-acceleration ($\Gamma$) of odorants out of the water, water-air and air partitions. These $\Omega$ values are used to separate the fragrance into so-called "water release groups", therefore predicting the chronological elution of odorants out the water, water/air into the air partitions.

$$\Omega = n\Phi\cdot\Gamma$$

Within these defined water-release groups, odorants are then further described based on their experimentally determined odor detection thresholds (ODT) and/or theoretically calculated "odor indices" to further characterize the odor impact or olfactive intensity along with the hedonic type of the released group of odorants. Defined "odor impact" within each water release group is discussed in depth later in this invention and serves to correlate mass transfer values of odorants and their detection thresholds to yield a measure of odor perception and odor contribution of each odorant within the water release groups.

Within these defined water-release groups, odorants are then further described based on their experimentally determined odor detection thresholds (ODT) and/or theoretically calculated odor indices to characterize their odor impact or their olfactive intensity along with the hedonic type of the released group of odorants considered. Careful design of the so-called "water release groups" in heavy aqueous dilutions based on odorants' water release values $\Omega$, enables a person skilled in the art to optimize the released perfume to have a linear and/or a delayed hedonic note.

A "linear sustained release" is defined as a continuous sustained release of a single perfume note throughout the rinse-off experience.

A "delayed release" of a perfume note during rinse-off process is defined by the appearance and/or a sudden change in perfume profile during the rinse-off process and/or the appearance of a single perfume note different from the overall hedonic profile preceding it.

Delayed release of odorants is typically attained by known methods using of various delivery methods such as encapsulation and other polymeric means. Various examples of encapsulation include the use of cyclodextrin, polymeric delivery vehicles, proteins etc. This invention enables the inventors to design perfumes with delayed release of various different odor profiles without the use of any encapsulation means, based solely of mass transfer properties and odor intensity of the odorants in the engineered perfume to be used in heavy water dilutions.

Perfume considered for rinse-off applications are optimized using different groups of odorants within the total perfume formula. These defined "water release groups" are explained in more details in the invention and their constituting odorants grouped are carefully chosen based on their odor intensity and mass transfer properties as described in the invention herein.

In addition to their water release values perfume odorants are further characterized according to their odor contribution within each "water release groups" based on their odor detection threshold values and/or their calculated odor indices.

Linear Release Perfumes for Rinse-Off

Fragrances or perfumes designed for "linear release" are based on odorants' water release $\Omega$, derived pseudo-acceleration $\Gamma$, odor detection threshold and/or odor index values in water and/or air as defined by the authors.

In addition, the following criteria need to hold true in order to achieve a linearly released fragrance note during rinse-off. The odorants used as part of the sustained linearly released fragrance note must contain at least three different odorants, which are part of the engineered sustained and linearly released perfume note. These at least three odorants must elute in at least three different "water release groups" based on odorants $\Omega$ values and as defined in the herein invention.

Additionally, at least one odorant contributing to the linear released perfume has a water release value of about 0.007 and greater (units of $$\left(\frac{\text{Force}}{\text{Area}}\right) \times \frac{1}{\text{time}}$$

as defined in this invention) or in other words, belonging to either Water release Groups: 1 and/or 2 and/or 3 as defined herein.

Additionally, at least one odorant contributing to the linear released perfume may have a derived pseudo-acceleration values $\Gamma$ of from about 100 to about 1000 (cm/sec$^2$), corresponding to sustained release value in water dilutions.

Additionally, at least one odorant contributing to the linearly released perfume may have an odor detection threshold in water value and/or an odor index in water value, as defined in the present invention of about 50 parts per billion and less.

Additionally, at least one odorant contributing to the linearly released perfume may have an odor detection threshold in air and/or odor index determined in air of about 0.025 mg/m$^3$ and less.

Delayed Release Perfumes for Rinse-Off

Perfumes engineered for "delayed release" of a fragrance note are constructed based on odorants' predicted elution behavior out of large water dilutions, simulating rinse-off conditions. These odorants release into headspace during rinse-off are predicted based on their water release $\Omega$ and derived pseudo-acceleration $\Gamma$ values. Their perceived intensity is in turn gauged by their odor detection threshold and/or odor index values in water and/or air as defined by the authors. The engineered fragrance key engineered for delayed release in rinse-off conditions contain at least two odorants, preferably at least three odorants, contributing to the delayed odor.

Each of the at least two odorants mentioned above, contributing to the delayed odor have a water release values lower than about 0.007 (units of $$\left(\frac{\text{Force}}{\text{Area}}\right) \times \frac{1}{\text{time}}$$

as defined in this invention), and therefore elute in rinse-off conditions as part of Water Release Groups 4 and/or 5 and/or 6 and preferably as part of Water Release Groups 5 and/or 6, or in other words, have a $\Omega$ value less than about 0.0005).

At least one odorant contributing to the delayed perfume character with characteristic odor intensity and water release properties mentioned above may have a derived pseudo-acceleration values $\Gamma$ of from about 100 to about 1000 (cm/sec$^2$), corresponding to sustained release in water dilutions.

At least one odorant contributing to the desired delayed odor may have an odor detection threshold in water value and/or an odor index in water value, as defined in the present invention of 50 parts per billion or less.

Additionally, at least one odorant contributing to the delayed release perfume may have an odor detection threshold in air and/or odor index determined in air of about 0.025 mg/m$^3$ and less.

Water based formulations are usually oil in water or water in oil emulsions with a varied concentration of water. By emulsifying these partitions, fragrances are dispersed and solubilized. Upon heavy water dilutions typical for the average household, industrial and cosmetic use, odorants making up perfumes need to diffuse through what is considered to be mostly water, a vapor phase above the liquid phase and finally the air phase.

Water Release Value, $\Omega$

To increase the water release impact of these fragrances in these systems, properties of odorants based on their mass transfer characteristics were used. These odorants' release properties in water ($\Omega_{1,2}$) will determine the order of elution of these odorants in the partitions considered: water, water-air and air.

$$\Omega = n\Phi \cdot \Gamma \qquad [1]$$

Φ=Flux of odorant in a system considering the partitions: water, water-air and air, expressed in $$\frac{mg}{cm^2 \times sec}$$

and Γ=Pseudo-acceleration factor of odorant in water, water-air and air expressed in $$\frac{cm}{sec^2};$$

n is the parts quantity of an odorant in a total 100 parts of a perfume.

This value of water release is indicative of the chronological order of elution of the odorants involved in the composition of the perfume diluted in water. As discussed later in this document, it is intimately linked to various thermodynamic and calculated mass transfer properties obtained by the authors but also based on quantity of the odorant considered within the entire formula. Below is the description of the terms used to derive equation [1].

Flux ($\Phi_{1,2}$)

Flux of an odorant in partitions water, water-air and air, (Φ) is defined as the ratio of the quantity of odorant being transferred in the media considered divided by the time and area of the contained medium. Flux values can also be defined in relation to a concentration gradient of the odorant throughout a partition according to:

$$\Phi_{12} = -D_{12}\left(\frac{d(c_1)}{dz}\right) \quad [2]$$

$D_{12}$ is the diffusion constant of odorant (1) in partition (2) and $$\left(\frac{d(c_1)}{dz}\right)$$

is the concentration gradient of odorant (1) throughout the partition. $D_{12}$ is calculated using the "Slattery Kinetic Theory" with non-polar odorants using odorants' critical parameters, unsteady state evaporation and measurement of binary diffusion coefficient. (Chem. Eng. Sci. 52, 1511-1515). The concentration gradients of the odorants composing the perfumes throughout the partitions considered (water, water-air and air) are calculated by solving for the dimensionless velocity value determined using the Arnold equation. (See Arnold, J. H. Studies in Diffusion: III. Unsteady State Vaporization and Absorption. Trans. Am. Inst. Chem Eng., 40, 361-378.).

Some flux values for a variety of odorants out of a water partition are listed in Table 1 below.

TABLE 1

| Odorant | Φ (mg/cm² · sec) |
|---|---|
| Ethyl 2-methylbutyrate | 0.004361536 |
| d-1-Methyl-4-isopropenyl-1-cyclohexene | 0.001571820 |
| 2,2-Dimethyl-3-(p-ethylphenyl)propanal | 0.000006157 |
| 4-Methyl-3-decen-5-ol | 0.000004491 |

TABLE 1-continued

| Odorant | Φ (mg/cm² · sec) |
|---|---|
| 5-Hexyldihydro-2(3H)-furanone | 0.000005070 |
| 1-(5,5-Dimethyl-1-cyclohexen-1-yl)-pent-4-en-1-one | 0.000005501 |
| 6,6-Dimethyl-2-methylenebicyclo-(3.1.1)-heptane | 0.001912106 |
| 6-sec-Butylquinoline | 0.000006754 |
| Octahydro-4,7-methano-1H-indene-5-yl acetate | 0.000009115 |
| Ethyl 2,3-epoxy-3-methyl-3-phenylpropionate | 0.000010182 |
| 2(6)-methyl-8-(1-methylethyl)-bicyclo[2.2.2] octe-5-en-2(3)-yl-1,3-dioxolane | 0.000003792 |
| Isopropyl-methyl-2-butyrate; | 0.002632239 |
| Tricyclo-decenyl propionate | 0.000003150 |
| 2,6,10-Trimethyl-9-undecenal | 0.000001843 |
| Methyl-2-hexyl-3-oxocyclopetanedecarboxylate | 0.000000204 |
| 2-Phenylethyl phenylacetate | 0.000000080 |
| 3,7-Dimethyl-1,6-octadien-3-yl 3-phenyl-2-propenoate | 0.000000039 |
| Ethyl octyne carbonate | 0.000007735 |
| 3,7-Dimethyl-2,6-octadien-1-thiol | 0.000046576 |
| (1R-(1a,4b,4aa,6b,8aa))-Octahydro-4,8a,9,9-tetramethyl-1,6-methano-1(2H)-naphtol | 0.000001119 |

Pseudo-Acceleration, Γ

In the analysis of the volatility of odorants, several variables are found to be important. First, the vapor pressure of the odorant is an important measure of its volatility. The product of the odorant's activity coefficient γ in the partition its mole fraction X and its pure vapor pressure value $P_v$, gives the odorant's relative vapor pressure. A second important factor for volatility is the diffusivity $D_{12}$ of the odorant in the considered media: water, vapor phase and subsequently air.

Other important variables to consider are the molecular weight $M_w$, of the odorant and its density in the partition $\rho_l$ and in the solvent vapor state $\rho_v$. The final variable to consider is an energy parameter in the partition state. The energy difference $\epsilon_{12} = \epsilon_{12(polar)} - \epsilon_{12o(non-polar)}$ is proportional to the partition coefficient of an odorant in a polar solvent such as water, and a water immiscible solvent such as octanol, benzene and paraffin liquid. The energy $\epsilon_{12}$ is called the partition energy and can be correlated to the clogP value of odorants. By definition: clogP proportional to $(\epsilon_{12(water)} - \epsilon_{12(octanol)})/R*T$; R=1.987 cal/(mole-° K); T=temperature (kelvin).

The five variables $D_{12}$, $P_v$, Mw, $\rho_v$ and $\epsilon_{12}$ and the three dimensional variables indicate that there can be 5−3=2 dimensional variables which describe Newton's law. The easiest separation is to break the acceleration vector into 2 dimensional quantities: a frequency or first order rate constant (1/time) and a velocity (distance/time) term.

The velocity group can be formed from the vapor pressure and density. Since pressure has units of mass*distance/distance²*time², and density has units of mass/distance³, the ratio of the two has units of velocity squared. The square root gives the desired velocity.

The first order rate constant can be formed from the variables Mw, $D_{12}$ and $\epsilon_{12}$. Since the partition energy $\epsilon_{12}$ has dimensions of calories per mole (mass.length²/mole.time²) and the diffusivity coefficient $D_{12}$ has a dimension of distance² per time, the ratio yields exactly a molecular weight unit per time t. The energy can be made dimensionless by dividing by the gas constant k and temperature T. The remaining variable $D_{12}$ can be made to a frequency by dividing by a cross sectional area $L^2$. A molecular area calculated from the liquid molar volume could represent this area.

Some Γ values for a variety of odorants are listed below in Table 2.

TABLE 2

| Odorant | Γ (cm/sec$^2$) |
|---|---|
| Ethyl 2-methylbutyrate | 12827.56 |
| d-1-Methyl-4-isopropenyl-1-cyclohexene | 8200.76 |
| 2,2-Dimethyl-3-(p-ethylphenyl)propanal | 121.17 |
| 4-Methyl-3-decen-5-ol | 116.38 |
| 5-Hexyldihydro-2(3H)-furanone | 115.36 |
| 1-(5,5-Dimethyl-1-cyclohexen-1-yl)-pent-4-en-1-one | 109.12 |
| 6,6-Dimethyl-2-methylenebicyclo-(3.1.1)-heptane | 9007.51 |
| 6-sec-Butylquinoline | 135.34 |
| Octahydro-4,7-methano-1H-indene-5-yl acetate | 144.06 |
| Ethyl 2,3-epoxy-3-methyl-3-phenylpropionate | 147.67 |
| 2(6)-methyl-8-(1-methylethyl)-bicyclo[2.2.2] octe-5-en-2(3)-yl-1,3-dioxolane | 57.74 |
| Isopropyl-methyl-2-butyrate; | 8722.05 |
| Tricyclo-decenyl propionate | 60.58 |
| 2,6,10-Trimethyl-9-undecenal | 43.58 |
| Methyl-2-hexyl-3-oxocylopetanedecarboxylate | 6.71 |
| 2-Phenylethyl phenylacetate | 2.29 |
| 3,7-Dimethyl-1,6-octadien-3-yl 3-phenyl-2-propenoate | 0.71 |
| Ethyl octyne carbonate | 156.29 |
| 3,7-Dimethyl-2,6-octadien-1-thiol | 659.09 |
| (1R-(1a,4b,4aa,6b,8aa))-Octahydro-4,8a,9,9-tetramethyl-1,6-methano-1(2H)-naphtol | 25.57 |

Pseudo acceleration values are also closely linked to the ability of an odorant to travel through headspace once it is airborne in addition to its ability to migrate through the water and water-air partitions. This value is predictive of what the authors consider "flash release", "sustained release" and "deposition" of odorants in heavy water dilutions.

"Flash release" is defined as fast migration through water and subsequent very low residence time in headspace, resulting in a short hedonic experience and very minimal deposition on a treated surface. "Sustained release" is characterized by good water release properties along with a longer residence time in the water vapor and subsequently, the air phase. "Deposition" is a term used to categorize odorants with very poor water release properties and consequently superior deposition on the surfaces treated. Flash release odorants are considered by the authors to have acceleration, Γ values above 900 cm/sec$^2$, sustained release odorants are thought to have Γ values between 900 and 100 and finally deposition odorants have acceleration values of less than 100.

As an illustration, some odorants with characteristic acceleration values for all three release categories defined by the authors are shown below. Water release properties are observed in 1 to 100 water dilution of a typical formulation containing these odorants as shown in the following procedure. The odorants chosen for this illustrative example are shown in Table 3.

TABLE 3

| | | Γ (acceleration water/air) |
|---|---|---|
| Flash Release | ethyl formate | 46183.23 cm/sec$^2$ |
| | ethyl-2-methyl butyrate | 12827.56 |
| | melonal | 2655.52 |
| | cyclacet | 1687.87 |
| Sustained Release | linalool | 644.41 |
| | aldehyde c-11 moa | 401.44 |
| | alpha ionone | 283.60 |
| | lilial | 104.63 |
| Deposition Odorants | cyclamen aldehyde | 99.64 |
| | jasmolactone | 76.30 |
| | hexyl cinnamic aldehyde | 21.01 |
| | acetal cd | 0.08 |

Experimental Procedure: Individual odorant to be tested was added to 20 g of shampoo formulation (see formula below in Table 4) at 0.1%.

TABLE 4

House Shampoo Formulation

| Phases | Ingredients | Supplier | Percent |
|---|---|---|---|
| A | D.I. Water | | 35.00 |
| A | Standapol ES-2 | Cognis Corp. | 35.00 |
| B | Standapol WAQ-LC | Cognis Corp | 27.50 |
| B | Glydant 2000 | Lonza | 0.30 |
| C | Sodium Chloride | | 1.80 |

A 10 gram sample of formulation and fragrance was added to an empty 1000 ml pyrex beaker. This beaker was then filled with 1000 ml of 120 F tap water. Beaker with diluted shampoo sample was then immediately placed into a semi-enclosed plexiglass chamber.

Headspace Sampling: Once beaker was placed into chamber a Carboxan SPME field fiber was held at the top-side opening of the chamber over the beaker containing the sample. At 15 seconds, the fiber was released and the headspace emissions from the beaker were collected. Headspace emissions from beaker were collected at 15, 30, 60, 90, 120, 240 and 300 seconds using a different Carboxan-PDMS field fiber for each sampling time. Top of plexiglass chamber was held open for entire 5 minutes of headspace sampling.

Each Carboxan-PDMS SPME Field Fiber that was used for each of the seven above sampling time intervals was then desorbed on a Hewlett Packard HP6890 GC/5973 Mass Selective Detector System.

Results are shown in FIG. 1, noting odorants residence time in headspace according to their Γ values.

Water Release Value, Ω

The partition release value Ω is defined as the product of the pseudo acceleration Γ and the flux value Φ and the quantity of odorant in a total 100 parts of the perfume diluted in water. The units of Ω are $$\left(\frac{mg \cdot cm}{cm^2 \cdot sec^2}\right) \cdot \frac{1}{sec}.$$

The expression of water release out of the water, water-air and air partitions can then be physically equated to a value of $$\left(\frac{Force}{Area}\right) \times \frac{1}{sec}$$

or in other words, units of pressure per time out partition. It is important to establish that water release values are indicative of the order of elution of odorants in a perfume out the partitions considered into headspace when subject to extreme aqueous dilutions. It is indicative of how fast in time will an odorant start to appear in time.

This predictive value for elution time allows a person skilled in the art to establish groupings of odorants eluting from the water dilutions, constructing therefore keys or hedonic profile and achieving better engineering control of their creative process. By engineering these groupings of odorants and their order of elution, a perfumer can construct optimized perfumes for water release systems, since most of these odorants will behave differently in aqueous dilutions as compared to emulsions with various surfactant proportions.

Water release values, Ω for the corresponding odorants is an indication of the time it will take before it appears in headspace when diluted in water. Once in headspace, acceleration values as well as odor detection thresholds (discussed in more details further) will dictate the intensity and odor contribution as well as residence time of odorants in the water vapor and air. The following relationships were empirically established by the authors for elution time of odorants in heavily diluted aqueous media based on Ω value ranges as shown in Table 5.

TABLE 5

Water Release Value Ranges

| | Water Release Values | Time of elution |
|---|---|---|
| Water Release Group 1 | Ω ≧ 10 | Upon dilution: t = 0 seconds |
| Water Release Group 2 | 10 > Ω ≧ 0.07 | 0 to 10 seconds |
| Water Release Group 3 | 0.07 > Ω ≧ 0.007 | 0 to 20 seconds |
| Water Release Group 4 | 0.007 > Ω ≧ 0.0005 | 0 to 30 seconds |
| Water Release Group 5 | 0.0005 > Ω ≧ 0.00003 | 0 to 45 seconds |
| Water Release Group 6 | 0.00003 > Ω | 0 to 60 seconds |

As an illustration, the below "Tropical Fruit" perfume release profile was observed in aqueous dilution of 1/100 using headspace GC-MS method at 1% in a house shampoo formulation (see formulation above).

The perfume's components are grouped in the predicted water release groups or ranges (1 to 6) according to the Ω values above along with the predicted time of elution (t) from the diluted aqueous/air partitions.

TABLE 6

Tropical Fruit Perfume

| | Parts | Ω |
|---|---|---|
| Predicted Water Release Group 1 [t = 0 seconds] | | |
| d-LIMONENE | 2 | 25.7802389895 |
| Predicted Water Release Group 2 [t less than 10 seconds] | | |
| ETHYL BUTYRATE | 0.1 | 7.0552312843 |
| ETHYL 2-METHYLBUTYRATE PURE FCC | 0.1 | 5.5947876874 |
| TRIPLAL | 0.3 | 4.1970000000 |
| MANZANATE | 0.1 | 0.5903646696 |
| LINALOOL | 9 | 0.2769314405 |
| DIHYDROMYRCENOL | 3 | 0.1905945812 |
| Predicted Water Release Group 3 [t less than 20 seconds] | | |
| ROSE OXIDE (HIGH CIS) | 0.1 | 0.0584040169 |
| CIS-3-HEXEN-1-OL | 0.2 | 0.0513223980 |
| BENZYL ACETATE | 1.3 | 0.0511546620 |
| CITRONELLOL AJ, FCC | 0.7 | 0.0405549107 |
| VERDOX | 2.5 | 0.0242936469 |
| ALLYL HEPTOATE | 0.5 | 0.0216167817 |
| ALDEHYDE C-18 | 0.5 | 0.0209445281 |
| CIS-3-HEXENYL ACETATE | 0.1 | 0.0180243127 |
| ETHYL LINALOOL | 2.9 | 0.0121483853 |
| BENZYL PROPIONATE | 0.5 | 0.0114915690 |
| FRUCTONE | 0.3 | 0.0103951730 |
| LIFFAROME | 0.1 | 0.0102830404 |
| DIHYDROLINALOOL | 0.2 | 0.0071934130 |
| Predicted Water Release Group 4 [t less than 30 seconds] | | |
| IONONE BETA PURE | 0.9 | 0.0066027260 |
| DIMETHYL BENZYL CARBINYL ACETATE | 1 | 0.0044592702 |
| VERTENEX HC | 0.1 | 0.0011211319 |

TABLE 6-continued

Tropical Fruit Perfume

| | Parts | Ω |
|---|---|---|
| TERPINYL ACETATE | 0.1 | 0.0010096117 |
| Predicted Water Release Group 5 [t less than 45 seconds] | | |
| FLOROL | 2.5 | 0.0004707520 |
| TERPINEOL | 0.1 | 0.0004502877 |
| OXANE | 0.01 | 0.0003278790 |
| UNDECAVERTOL | 0.6 | 0.0003136174 |
| FLORHYDRAL | 0.3 | 0.0002988038 |
| ALLYL CYCLOHEXYL PROPIONATE | 0.3 | 0.0002838164 |
| HEXYL CINNAMIC ALDEHYDE | 15 | 0.0002445428 |
| GAMMA-DECALACTONE | 0.3 | 0.0001754522 |
| GAMMA UNDECALACTONE | 0.3 | 0.0001426688 |
| alpha-DAMASCONE | 0.1 | 0.0001360916 |
| MAGNOLAN/CORPS 719 | 3 | 0.0001281900 |
| HELIONAL | 1.4 | 0.0000393253 |
| ADOXAL | 0.4 | 0.0000321258 |
| BENZYL ALCOHOL | 0.2 | 0.0000319302 |
| BACDANOL | 1.5 | 0.0000316677 |
| Predicted Water Release Group 6 [t less than 60 seconds] | | |
| HEDIONE | 15 | 0.0000209666 |
| SANDALORE | 1.3 | 0.0000177176 |
| DAMASCENONE | 0.03 | 0.0000147507 |
| GALAXOLIDE 50 IPM | 5 | 0.0000144162 |
| CALONE | 0.03 | 0.0000057982 |
| AMBROXAN | 0.03 | 0.0000012314 |
| ETHYLENE BRASSYLATE | 4.3 | 0.0000012189 |
| OXANONE CRYSTALS | 0.4 | 0.0000010442 |
| VERTOFIX COEUR | 0.1 | 0.0000004524 |
| EXALTOLIDE TOTAL | 0.2 | 0.0000002980 |
| METHYL ATRATATE | 0.1 | 0.0000000003 |
| | 79.1 | |
| propylene glycol | 20.9 | |
| total perfume | 100 | |

Below in Table 7 are the experimental results for the release profile in time (0 to 60 seconds) of the Tropical Fruit Perfume in 1/100 dilution in water using GC-MS headspace analysis.

TABLE 7

| | GC Abundance |
|---|---|
| 5 seconds | |
| d-LIMONENE | 7000 |
| 10 seconds | |
| d-LIMONENE | 7000 |
| ETHYL 2-METHYLBUTYRATE | 3000 |
| ETHYL BUTYRATE | 2800 |
| TRIPLAL | 1000 |
| MANZANATE | 1000 |
| LINALOOL | 500 |
| DIHYDROMYRCENOL | 500 |
| 20 seconds | |
| d-LIMONENE | 7000 |
| TRIPLAL | 14000 |
| ETHYL BUTYRATE | 2800 |
| ETHYL 2-METHYLBUTYRATE PURE FCC | 3100 |
| MANZANATE | 4000 |
| LINALOOL | 18000 |
| DIHYDROMYRCENOL | 15000 |
| ROSE OXIDE (HIGH CIS) | 10000 |
| CIS-3-HEXEN-1-OL | 14000 |
| BENZYL ACETATE | 12000 |
| CITRONELLOL AJ, FCC | 7000 |
| VERDOX | 5000 |
| ALLYL HEPTOATE | 4000 |
| ALDEHYDE C-18 | 2000 |

TABLE 7-continued

| | GC Abundance |
|---|---|
| CIS-3-HEXENYL ACETATE | 5000 |
| ETHYL LINALOOL | 5000 |
| BENZYL PROPIONATE | 2000 |
| FRUCTONE | 3000 |
| LIFFAROME | 3000 |
| DIHYDROLINALOOL | 3000 |
| 30 seconds | |
| d-LIMONENE | 7000 |
| TRIPLAL | 14000 |
| ETHYL BUTYRATE | 2800 |
| ETHYL 2-METHYLBUTYRATE PURE FCC | 3100 |
| MANZANATE | 4000 |
| LINALOOL | 18000 |
| DIHYDROMYRCENOL | 15000 |
| ROSE OXIDE (HIGH CIS) | 14000 |
| CIS-3-HEXEN-1-OL | 14000 |
| BENZYL ACETATE | 17000 |
| CITRONELLOL AJ, FCC | 7000 |
| VERDOX | 14000 |
| ALLYL HEPTOATE | 10000 |
| ALDEHYDE C-18 | 2000 |
| CIS-3-HEXENYL ACETATE | 14000 |
| ETHYL LINALOOL | 10000 |
| BENZYL PROPIONATE | 6000 |
| FRUCTONE | 5000 |
| LIFFAROME | 3000 |
| DIHYDROLINALOOL | 3000 |
| IONONE BETA PURE | 2000 |
| DIMETHYL BENZYL CARBINYL ACETATE | 2000 |
| VERTENEX HC | 2000 |
| TERPINYL ACETATE | 1000 |
| 40 seconds | |
| d-LIMONENE | 5000 |
| TRIPLAL | 10000 |
| ETHYL BUTYRATE | 2000 |
| ETHYL 2-METHYLBUTYRATE PURE FCC | 2000 |
| MANZANATE | 3000 |
| LINALOOL | 18000 |
| DIHYDROMYRCENOL | 15000 |
| ROSE OXIDE (HIGH CIS) | 14000 |
| CIS-3-HEXEN-1-OL | 14000 |
| BENZYL ACETATE | 18000 |
| CITRONELLOL AJ, FCC | 7000 |
| VERDOX | 18000 |
| ALLYL HEPTOATE | 12000 |
| ALDEHYDE C-18 | 4000 |
| CIS-3-HEXENYL ACETATE | 14000 |
| ETHYL LINALOOL | 10000 |
| BENZYL PROPIONATE | 6000 |
| FRUCTONE | 5000 |
| LIFFAROME | 3000 |
| DIHYDROLINALOOL | 3000 |
| IONONE BETA PURE | 10000 |
| DIMETHYL BENZYL CARBINYL ACETATE | 8000 |
| VERTENEX HC | 8000 |
| TERPINYL ACETATE | 9000 |
| FLOROL | 10000 |
| TERPINEOL | 10000 |
| OXANE | 2000 |
| UNDECAVERTOL | 10000 |
| FLORHYDRAL | 9000 |
| ALLYL CYCLOHEXYL PROPIONATE | 7000 |
| HEXYL CINNAMIC ALDEHYDE | 2000 |
| GAMMA-DECALACTONE | 4000 |
| GAMMA UNDECALACTONE | 4000 |
| alpha-DAMASCONE | 1000 |
| MAGNOLAN/CORPS 719 | 1000 |
| HELIONAL | 500 |
| ADOXAL | 300 |
| BENZYL ALCOHOL | 50 |
| BACDANOL | 100 |
| 50 seconds | |
| d-LIMONENE | 4000 |
| TRIPLAL | 6000 |
| ETHYL BUTYRATE | 800 |
| ETHYL 2-METHYLBUTYRATE PURE FCC | 1500 |
| MANZANATE | 1500 |
| LINALOOL | 18000 |
| DIHYDROMYRCENOL | 15000 |
| ROSE OXIDE (HIGH CIS) | 14000 |
| CIS-3-HEXEN-1-OL | 14000 |
| BENZYL ACETATE | 18000 |
| CITRONELLOL AJ, FCC | 7000 |
| VERDOX | 20000 |
| ALLYL HEPTOATE | 12000 |
| ALDEHYDE C-18 | 4000 |
| CIS-3-HEXENYL ACETATE | 14000 |
| ETHYL LINALOOL | 10000 |
| BENZYL PROPIONATE | 6000 |
| FRUCTONE | 5000 |
| LIFFAROME | 3000 |
| DIHYDROLINALOOL | 3000 |
| IONONE BETA PURE | 18000 |
| DIMETHYL BENZYL CARBINYL ACETATE | 8000 |
| VERTENEX HC | 10000 |
| TERPINYL ACETATE | 9000 |
| FLOROL | 15000 |
| TERPINEOL | 15000 |
| OXANE | 2000 |
| UNDECAVERTOL | 10000 |
| FLORHYDRAL | 10000 |
| ALLYL CYCLOHEXYL PROPIONATE | 10000 |
| HEXYL CINNAMIC ALDEHYDE | 9000 |
| GAMMA-DECALACTONE | 7000 |
| GAMMA UNDECALACTONE | 7000 |
| alpha-DAMASCONE | 5000 |
| MAGNOLAN/CORPS 719 | 3000 |
| HELIONAL | 5000 |
| ADOXAL | 3000 |
| BENZYL ALCOHOL | 100 |
| BACDANOL | 5000 |
| GALAXOLIDE 50 IPM | 1000 |
| HEDIONE | 4000 |
| SANDALORE | 2000 |
| DAMASCENONE | 1000 |
| CALONE | 1000 |
| AMBROXAN | 1000 |
| ETHYLENE BRASSYLATE | 20 |
| OXANONE CRYSTALS | 70 |
| VERTOFIX COEUR | 50 |
| EXALTOLIDE TOTAL | 50 |
| METHYL ATRATATE | 50 |

Odorants making up the perfume eluted in a 1/100 water dilution as predicted by their calculated Ω values. For example, when considering the first 20 seconds of the release profile of the diluted perfume, the inventors predicted d-limonene to elute first based on its Ω value (Water Release Group 1). The headspace experiment confirmed the above calculated prediction.

The next group of odorants predicted to elute from the diluted partition (Water Release Group 2) was made of: triplal, ethyl butyrate, ethyl-2-methyl butyrate, manzanate, linalool and dihydromyrcenol at time less than 10 seconds. This second "wave" of released odorants will enter the headspace above the aqueous dilution in a background of "d-limonene", a flash release citrus note released earlier. This assumption was again validated by the experimental GC-MS headspace experiment.

The third group of odorants predicted to elute at time less than 20 seconds was expected to be rose oxide, cis-3-hexenol, benzyl acetate, citronellol, verdox, allyl heptoate, aldehyde C-18, cis-3-hexenyl acetate, ethyl linalool, benzyl propionate, fructone, liffarome and dihydrolinalool based on their Ω values. In the background, odorants making up water release groups 1 and 2 are present. This theoretical prediction is again validated by the GC MS headspace experimental data. All other odorants making up the subsequent release profile of the perfume are also accurately predicted based on odorants' W values as shown in the experimental data above. A person skilled in the art can, as a result use the invention to engineer the perceived progression of the fragrance in time as it is liberated from the aqueous dilution.

Odor Detection Thresholds

Upon their release in headspace, odorants are detected based on their odor detection threshold values. Odor detection thresholds are defined as the lowest concentration of odorants in a selected medium (air or water) to be detected. By including odor index values of odorants in the model, one can further improve on the values for predicted performance of once odorants are released from the partition into the air.

It is also important to construct the fragrance with a balanced olfactive intensity in order not to overwhelm the consumer or to be aesthetically unappealing. Constructing each segment for the targeted application or intended effect must be based on balanced impact in accordance to these ODT values while at the same time answering to certain rules to give a well-rounded experience to the consumer.

Various databases for experimental odor detection threshold values in various partitions such as water and air are available. See Compilation of Odor and Taste Threshold Values Data, American Society for Testing and Materials, F. A. Fazzalari Editor; Booleans Aroma Chemical Information Service (BACIS)).

In this invention, Odor Index (O.I.) values are calculated theoretically for odorants in air. These odor index values show a strong correlation with experimental odor detection thresholds in air and in water as shown later in this patent.

An example of how the inventors calculate mathematically these odor indices, the conformation of 1-undecanal deduced from docking experiments into $hOBP_{II\alpha}$ is used below.

a. Modeling of $hOBP_{II\alpha}$ Binding Site and Odorant Docking Experiments

Figure 2:
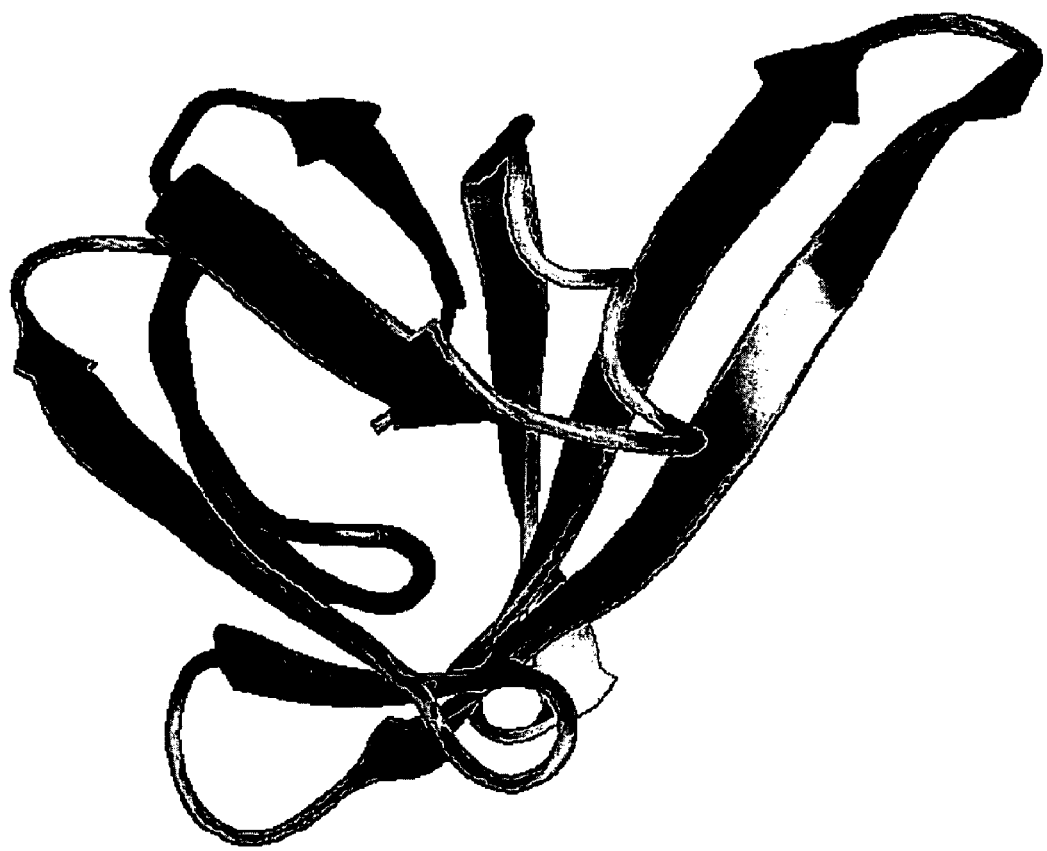
FIG. 2 shows the predicted tertiary structure for $hOBP_{II\alpha\alpha}$.

Human odorant binding protein $hOBP_{II\alpha}$ (17.8 kDa), belongs to the Lipocalin family. The amino acid sequence is 45.5% similar to the rat OBPII and 43% similar to the human tear lipocalin (TL-VEG). The tertiary structure of hOBPIIα was obtained using the automated SWISS-MODEL protein modeling service (http://swissmodel.expasy.org/). The modeled structure along with the modeled protein binding site is shown in FIG. 2, the predicted tertiary structure for $hOBP_{II\alpha}$. The eight-stranded β-barrel, a common motif for lipocalins is present as well as two alpha helices (as also predicted by Lacazette et al., Human Molecular Genetics, 2000, 9, 2, 289-301).

Figure 3:
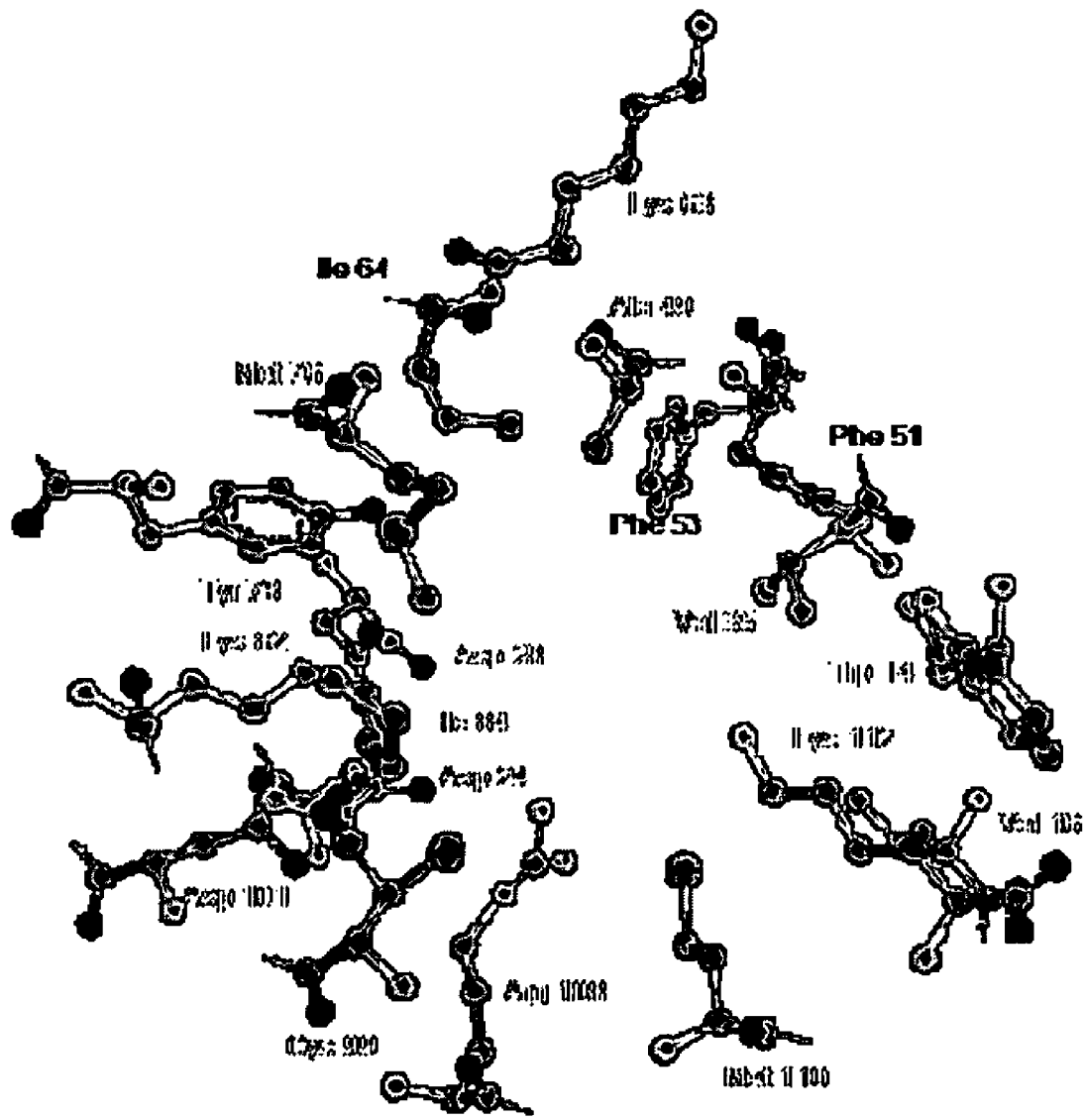
FIG. 3 shows the modeled binding site for $hOBP_{II\alpha\alpha}$.

FIG. 3 shows modeled binding site for $hOBP_{II\alpha}$. The conserved hydrophobic amino acids described by Lacazette et al. and thought to interact with ligands are shown.

Figure 4:
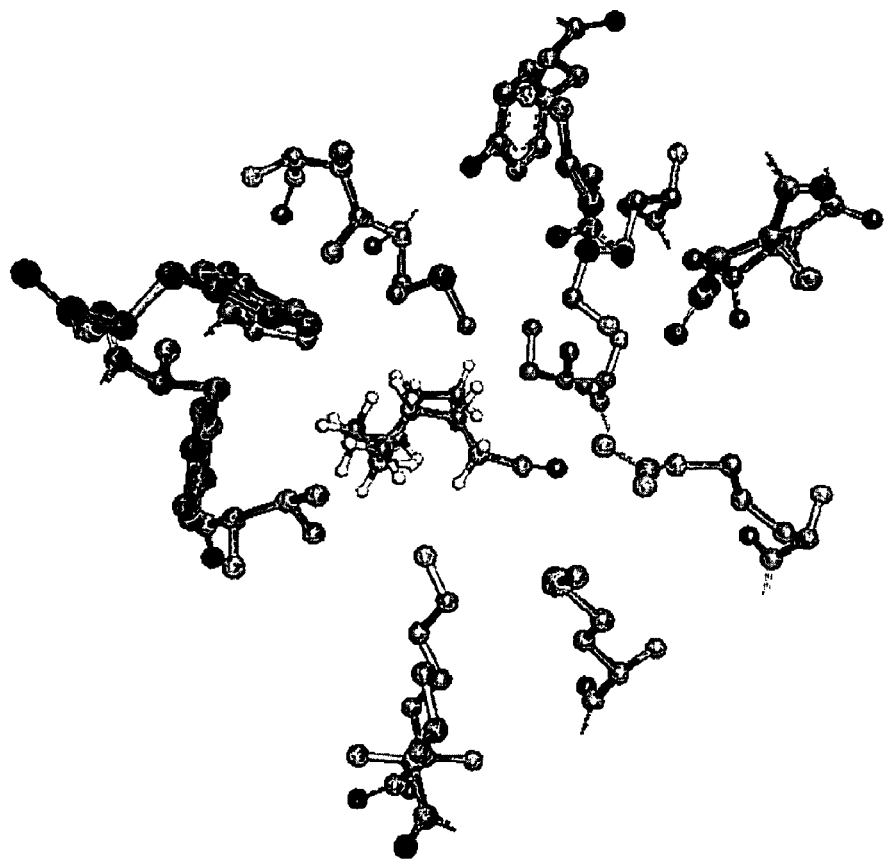
FIG. 4 is shows a docked conformation of 1-undecanal in the $hOBP_{II\alpha\alpha}$ binding cavity

FIG. 4 shows a docked conformation of 1-undecanal in the $hOBP_{II\alpha}$ binding cavity using a box size of 19×19.75×15.5 angstroms. The pose shown has docking energy of −10.05 kcal/mol. As an example, 1-undecanal was docked into the binding cleft of $hOBP_{II\alpha}$ using Argus lab software 4.0.1. in order to obtain the recognized conformation of the odorant (http://www.planaria-software.com/arguslab40.htm). The docked conformation of 1-undecanal within the binding cleft of the hOBP is show in FIG. 4.

Figure 5:
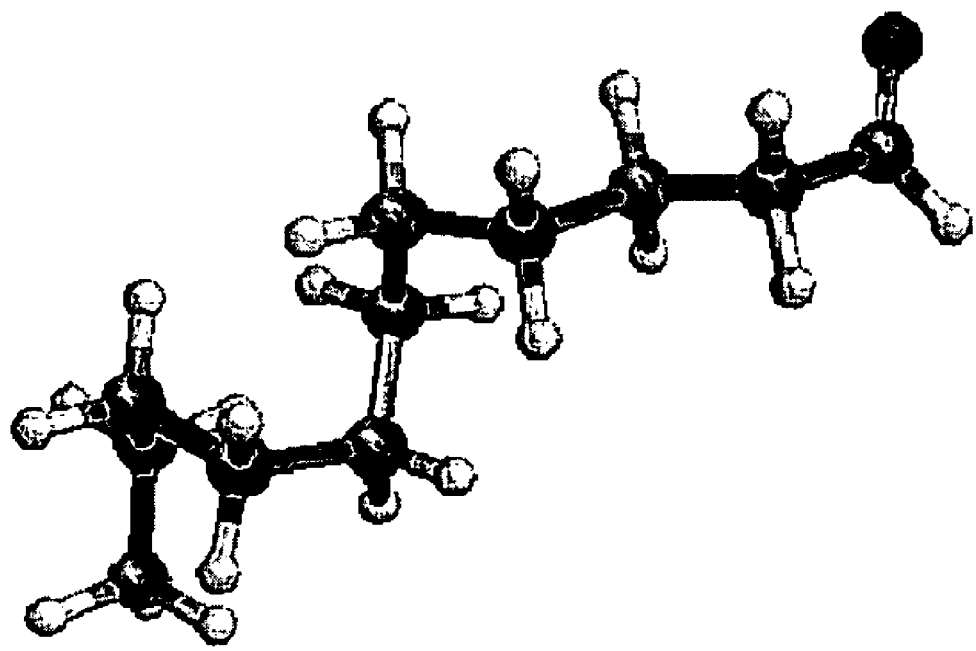
FIG. 5 shows the confirmation of 1-Undecanal used in odor index calculation.

FIG. 5 shows 1-Undecanal Conformation used in odor index calculation: the conformation for 1-undecanal was deduced from docking experiment into the binding cleft of $hOBP_{II\alpha}$. The most energetically favored conformation for 1-undecanal is shown in FIG. 10. This conformation is the used to calculate the maximum moment of inertia using a mathematical model of inertial ellipse.

b. Odor Index Calculation

Moment of Inertia

The inertial ellipse (which is fixed in the rigid body) rolls and reorients on the invariable plane. The path followed on the plane is called the herpolhode. The tip of the vector on the inertial ellipse in which the total angular momentum L is normal rotates on the ellipse to form a path called the polhode. The polhode is the property of the odorant molecule. The invariable plane is a hypothetical plane external to the molecule, which can "fit" into the receptor. The herpolhode is a curve on a surface defining a receptor site "geometry". The height in which the inertial ellipse sits above the plane is inversely related to the ratio of rotational/translational forces.

The inertial ellipse incorporates the moment of inertia and angular momentum (L) of the odorant in the reference frame in which L is fixed in space.

Translational/Rotational Constant

The translational/rotational constant is a ratio of translational to rotational energy. This factor is found to correlate to the type of functional group and most importantly to the Lydersen critical property increments.

Conformation of 1-undecanal shown in FIG. 11 was used to calculate the odor index value of 1-undecanal both in air and in water as an illustrative example. The odor index value in air was found to be equal 0.000219 mg/m$^3$. The experimental value for odor detection threshold in air was determined to be 0.00054 mg/m$^3$ by Randenbrock (See Randebrock, R. E. (1986) Perfuem. Kosmet. 67, 1, 10-24). Calculated odor index in water was calculated to be equal to 8.2 parts per billion (ppb), and found to be within the experimental range determined by Schnabel et al. (Schnabel, K. O. Belitz, H. D., Von Ranson, C. (1988) Lebensm. Unters. Forsch. 187, 215-223).

Odor Index Calculation for Various Odorants

The model and algorithm for odor index calculation was further applied to odorants from various chemical classes. The correlation results with published experimental odor detection thresholds as seen in FIG. 6.

Figure 6:
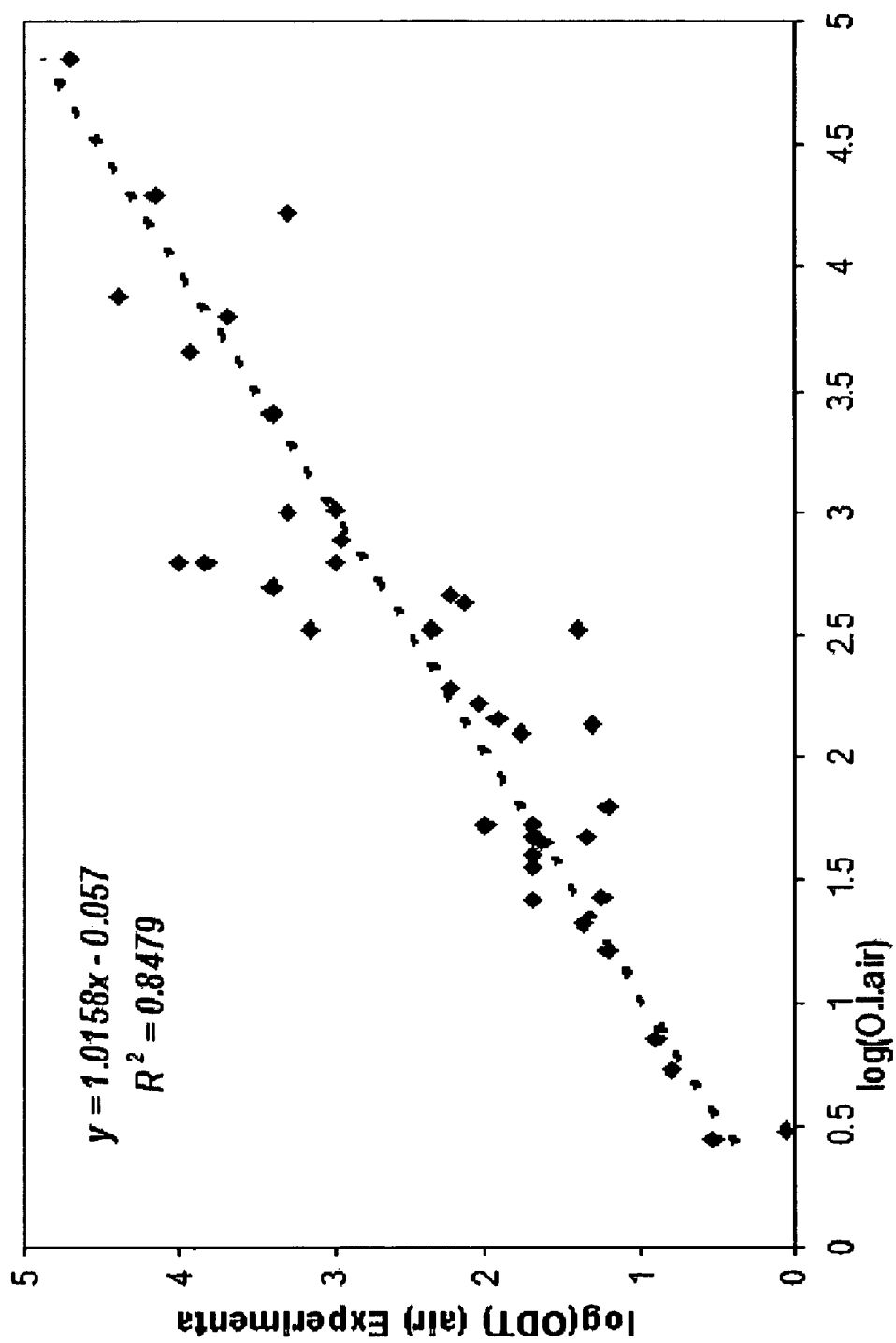
FIG. 6 is a graph showing the correlation between the experimental odor detection threshold values and calculated odor indices of various odorants.

FIG. 6 shows the correlation between the experimental odor detection threshold values from the "Compilations of Odor Threshold Values in Air" from the Booleans Aroma Chemical Information Service (BACIS) and calculated odor indices of various odorants. (All values are shown in mg/m$^3$.)

Odor Index values can also be calculated in water by correlating the activity of the odorants in a water partition and well as their diffusivity in the water, water-air and air partitions. These calculation results are shown below in Table 8 for some odorants and are correlated with experimental values from the Booleans database for experimental odor detection thresholds in water.

TABLE 8

| Name of Odorant | exp ODT (ppb) water | O.I. (ppb) Water |
|---|---|---|
| Butyl acetate | 44-88 | 118.00 |
| 2,6-Dimethyl-2,6-octadien-8-ol | 1-10 | 5.00 |
| trans-3,7-Dimethyl-2,6-octadien-1-yl propanoate | 10 | 2.00 |
| I-1-Methyl-4-isopropenyl-6-cyclohexen-2-one | 50 | 22.00 |
| 4-(2,2,6-Trimethyl-2-cyclohexen-1-yl)-3-buten-2-one | 0.4-10 | 2.5 |
| 4-Hydroxy-3-methoxybenzaldehyde | 25-58 | 27.53 |
| Ethyl butyrate | 1 | 5 |
| 4-(2,2,6-Trimethyl-2-cyclohexen-1-yl)-3-buten-2-one | 0.4-10 | 2.5 |
| 1-(2,6,6-Trimethylcyclohexa-1,3-dienyl)-2-buten-1-one | 0.002 | 0.009 |
| Pentyl butyrate | 44-87 | 68 |
| cis-3-hexenol | 39 | 25 |
| Ethyl 2-methylpentanoate | 0.0030 | 0.001 |
| α-1-(2,6,6-Trimethyl-2-cyclohexen-1-yl)-2-buten-1-one | 1.5 | 1.50 |
| 4-(2,6,6-Trimethyl-1-cyclohexen-1-yl)-3-buten-2-one | 4-6 | 2 |
| ethyl 2-methylbutyrate | 0.1-0.3 | 0.1 |
| 1-Hydroxy-2-methoxy-4-propenylbenzene | 30-40 | 40.00 |
| 2,6-Dimethyl-5-heptenal | 16 | 24 |
| 1-Octanal | 30 | 33 |
| Tetrahydro-4-methyl-2-(2-methylpropen-1-yl)pyran | 0.5 | 4 |
| 4-Hydroxy-3-methoxybenzaldehyde | 20-200 | 28 |
| Pentyl Acetate | 43 | 72 |
| Ethyl methylphenylglycidate | 25 | 3 |
| 5-Methyl-2-isopropylphenol | 400 | 306 | during rinse-off will contain only d-limonene as shown below in Table 9.

TABLE 9

Water Release Group 1

| | parts | Γ (cm/sec2) | Odor Impact | % Odor Contribution | Hedonic Profile |
|---|---|---|---|---|---|
| d-LIMONENE | 2.00 | 8200.76 | 34.00 | 100.00 | lemon-like |

Based on its Γ value, d-limonene is typical of a flash release material. In addition, the odor detection of odor detection threshold of d-limonene is not exceptionally when compared to odorants such as ethyl-2-methyl butyrate. Therefore, d-limonene is considered to be a typical "flash release material" in rinse-off conditions.

The next water release group as predicted earlier in this document is thought to be the following composition shown in Table 10.

TABLE 10

Water Release Group 2

| | parts | Γ (cm/sec2) | Odor Impact | % Odor Contribution | Hedonic Profile |
|---|---|---|---|---|---|
| TRIPLAL | 0.30 | 1696.11 | 0.02 | 0.02 | green slightly herbaceous citrus note |
| ETHYL BUTYRATE | 0.10 | 14612.29 | 0.02 | 0.02 | banana pineapple |
| ETHYL 2-METHYLBUTYRATE | 0.10 | 12827.56 | 1.00 | 0.97 | green fruit apple peel |
| MANZANATE | 0.10 | 5288.42 | 100.00 | 97.06 | fruity apple |
| LINALOOL | 9.00 | 644.41 | 1.80 | 1.75 | flowery fresh lily of the valley |
| DIHYDROMYRCENOL | 3.00 | 866.55 | 0.19 | 0.18 | fresh lime, overall citrus flower |

Perfume Odorants' Odor Impact and Contribution

Within each "water release group" odorant's defined odor impact is given by the following mathematical equation:

$$\text{odor impact} = \frac{\text{odorants parts(in 100 total perfume parts)}}{\text{odor detection threshold}} \quad [3]$$

The odor detection threshold (experimental values) for the odorants can also be substituted by their odor index values (theoretically calculated). Once the odor impact is determined, odorants percent odor contribution within the "overall water release" perfume profile can also be determined. As an example, the "tropical fruit perfume" will be used to determine the odor contribution of each odorant within the formula and their contribution within the rinse-off profile of the entire perfume. The "water release groups" determined according to the odorants' Ω values and further predicted to release in time based on values shown earlier in this invention are as follow.

According to the odorants Ω values, the "Water Release Group 1" thought to elute immediately upon water dilution The "water release group 2" is predicted to be fruity with mostly an apple character due to the very large contribution of manzanate to the overall odor profile of this group of odorants, which elute together from the water dilution. Most of the odorants within "Water Release Group 2" are considered "flash release" compounds based solely on their Γ values. It is important to emphasize the contribution of the odor index and/or odor detection values in addition to the Γ values when gauging flash release. For example, ethyl-2-methyl butyrate and manzanate despite their very high Γ values will have the tendency to be perceived longer when entering headspace since their odor detection thresholds are very low and need not to be present in high amounts to be recognized by a consumer.

If one were to build an emphasis on the hedonic note delivered in the next "Water Release Group 3", it would be important to take in consideration odor detection values of "Water Release Group 2" in order not to take away from the odorants delivered in Water Release Group 3. Populating Water Release Group 2 with odorants with high odor detection threshold or odor index values will therefore help emphasize the subsequent contribution of odorants eluting in Water Release Group 3, especially if these latter odorants have much higher odor impact (or lower odor detection threshold and odor index values).

the β-ionone odor contribution (violet). Due to its low odor detection threshold and/or odor index, β-ionone will have a tremendous impact to the overall fragrance once it is eluted in

TABLE 11

Water Release Group 3

| | parts | $\Gamma(cm/sec^2)$ | Odor Impact | Odor Contribution % | Hedonic Profile |
|---|---|---|---|---|---|
| ROSE OXIDE | 0.10 | 6219.26 | 0.0250 | 1.83 | geranium and carrot leaves |
| CIS-3-HEXEN-1-OL | 0.20 | 1569.11 | 0.0080 | 0.59 | fresh cut grass |
| BENZYL ACETATE | 1.30 | 664.29 | 0.0448 | 3.29 | jasmine gardenia |
| CITRONELLOL AJ, FCC | 0.70 | 868.56 | 0.0117 | 0.86 | rose-like |
| VERDOX | 2.50 | 564.56 | 0.2273 | 16.66 | fruity agrumen |
| ALLYL HEPTOATE | 0.50 | 711.58 | 0.2000 | 14.66 | fruity banana |
| ALDEHYDE C-18 | 0.50 | 292.22 | 0.1667 | 12.22 | coconut |
| CIS-3-HEXENYL ACETATE | 0.10 | 1384.27 | 0.0049 | 0.36 | green |
| ETHYL LINALOOL | 2.90 | 275.63 | 0.0354 | 2.59 | floral |
| BENZYL PROPIONATE | 0.50 | 522.41 | 0.0122 | 0.89 | sweet fruity |
| FRUCTONE | 0.30 | 554.79 | 0.6000 | 43.98 | green apple- |
| LIFFAROME | 0.10 | 1515.54 | 0.0063 | 0.46 | green fruity floral |
| DIHYDROLINALOOL | 0.20 | 568.81 | 0.0222 | 1.63 | fresh floral citrus |

According to the above values, the next released group of odorants will result in tropical fruit and slightly floral green undertones. This accord will elute in a background of apple note from Water Release Group 2 and a disappearing citrus note from Water Release Group 1.

The next "Water Release Group 4" will have the following composition and characteristic odor profile shown in Table 12.

headspace. B-ionone's Γ values, coupled with a very low odor detection threshold, result in a hedonic contribution and perceived for the rest of the rinse-off experience by the consumer.

The next fragrance accord to be released during rinse-off when using the Tropical Fruit Perfume is predicted to be that shown in Table 13.

TABLE 12

Water Release Group 4

| | Parts | $\Gamma (cm/sec^2)$ | Odor Impact | Odor Contribution % | Hedonic Profile |
|---|---|---|---|---|---|
| IONONE BETA PURE | 0.90 | 311.32 | 90.0000 | 99.58 | woody violet |
| DIMETHYL BENZYL CARBINYL ACETATE | 1.00 | 249.93 | 0.3636 | 0.40 | fresh green floral fruity |
| VERTENEX HC | 0.10 | 357.12 | 0.0118 | 0.01 | woody |
| TERPINYL ACETATE | 0.10 | 613.44 | 0.0004 | 0.00 | bergamot lavender |

According to the Γ values of the odorants within Water Release Group 4, this accord will be mostly characterized by

TABLE 13

Water Release Group 5

| | parts | $\Gamma (cm/sec^2)$ | Odor Impact | Odor Contribution % | Hedonic Profile |
|---|---|---|---|---|---|
| FLOROL | 2.50 | 63.16 | 0.5000 | 8.58 | floral |
| TERPINEOL | 0.10 | 269.84 | 0.0004 | 0.01 | lilac |
| OXANE | 0.01 | 610.16 | 0.0050 | 0.09 | passion fruit and grapefruit |
| UNDECAVERTOL | 0.60 | 116.38 | 0.3000 | 5.15 | green floral violet leaf like |
| FLORHYDRAL | 0.30 | 180.11 | 0.0333 | 0.57 | green floral lilly of the valley |
| ALLYL CYCLOHEXYL PROPIONATE | 0.30 | 126.80 | 0.3000 | 5.15 | pineapple |
| HEXYL CINNAMIC ALDEHYDE | 15.00 | 21.01 | 0.4286 | 7.35 | jasmine |
| GAMMA-DECALACTONE | 0.30 | 115.36 | 0.6000 | 10.29 | peach |
| GAMMA UNDECALACTONE | 0.30 | 42.98 | 1.0000 | 17.15 | peach |
| alpha-DAMASCONE | 0.10 | 157.30 | 0.0810 | 1.39 | fruity floral |
| MAGNOLAN | 3.00 | 31.03 | 1.5000 | 25.73 | magnolia grapefruit |
| HELIONAL | 1.40 | 25.40 | 0.2800 | 4.80 | green floral |
| ADOXAL | 0.40 | 43.58 | 0.0500 | 0.86 | floral |
| BENZYL ALCOHOL | 0.20 | 24.56 | 0.0015 | 0.03 | floral |
| BACDANOL | 1.50 | 25.13 | 0.7500 | 12.87 | sandalwood |

The accord released within the Water Release Group 5 can be described as being mostly fruity (peach and grapefruit) with a floral background. Odorants such as Oxane, considered a top note can be delivered much later during the rinse off process by carefully choosing the right dilution and based on its water release value, Ω. Conversely, using much higher concentrations of gamma-undecalactone will move its elution time much earlier into the earlier "Water Release Groups". Forcing odorants, such as gamma-decalactone with low odor detection threshold and low Γ values, to elute earlier by overdosing on their concentration within the perfume total will lead to a much sustained peach note that will last throughout the rinse-off once it is released into headspace.

The last predicted "Water Release Group 6" is shown below in Table 14.

TABLE 14

Water Release Group 5

| | parts | Γ (cm/sec$^2$) | Odor Impact | Odor Contribution % | Hedonic Profile |
|---|---|---|---|---|---|
| GALAXOLIDE 50 IPM | 5 | 7.49 | 1.0000 | 14.58 | musk |
| HEDIONE | 15 | 8.40 | 0.6000 | 8.75 | fruity jasmine |
| SANDALORE | 1.3 | 19.92 | 0.8667 | 12.64 | sandalwood |
| DAMASCENONE | 0.03 | 100.79 | 3.3333 | 48.60 | rose |
| CALONE | 0.03 | 55.448484 | 0.0030 | 0.04 | fresh marine |
| AMBROXAN | 0.03 | 20.559713 | 0.0600 | 0.87 | ambergris |
| ETHYLENE BRASSYLATE | 4.3 | 2.5579748 | 0.8600 | 12.54 | Musk |
| OXANONE CRYSTALS | 0.4 | 41.247051 | 0.0800 | 1.17 | rasberry |
| VERTOFIX COEUR | 0.1 | 10.136257 | 1.0000 | 14.58 | woody |
| EXALTOLIDE TOTAL | 0.2 | 5.8280534 | 0.0500 | 0.73 | Musk |
| METHYL ATRATATE | 0.1 | 0.1457731 | 0.0063 | 0.09 | Moss |

The Tropical Fruit perfume upon dilution gives the following fragrance profile during rinse-off, in particular shampoo, conditioner and body-wash applications as specified in Table 15.

TABLE 15

Perfume Released

Citrus tangerine
Green apple - tropical
Violet
Tropical fruit papaya
Floral musk Applied Perfume Examples This invention pertains to the engineering of hedonics based on mass transfer values of odorants making up a fragrance used in a rinse-off product. When including a particular natural or synthetic extract as a benefit agent in a product, part of the marketing strategy is to give the impression that the benefit is fully delivered by linking the smell of the water released product to the advertised benefit agent. The resulting release hedonics can be either sustained during the entire wash experience or can be engineered to appear at a specific moment starting from the beginning of the experience, or in other words delayed release.

In the first case, populating each release group described in this invention with an odorant that translates the desired note synonymous with the benefit agent for example will result in an impactful well rounded linear and sustained hedonic release of the desired odor.

For example, when considering a wash-off product targeted for dishwashing products, giving the impression of a sustained release of a particular fragrance note can be achieved by including a characteristic odorant in each considered water release groups. When including an apple odorant in water-release groups 1, 2, and 3 in rinse-off products according to the rationale discussed above, the consumer is able to have a maximized and sustained olfactory profile of the engineered fragrance note within the perfume released from water (apple in this case).

More preferably by including certain desired odorants with the same fragrance profile and an odor detection threshold of less than 50 ppb in four out of six targeted water release groups relative to the intended product, the inventors are able to maximize the impact of the delivered fragrance note upon water release.

As an illustrative example, the inventors have designed an apple fragrance for shampoo, body wash and conditioners that will give the consumer a sustained apple fragrance during the entire wash-off experience. Each water-release groups composing the perfume are shown below.

The inventors use the definition of odor impact to illustrate the applications of odor indices as a tool to predict the overall odor profile of each Water Release Group for the Apple fragrance. An apple odorant is present in five out of six release group in the perfume considered for this particular application by the inventors (water release groups 1, 2, 3, 4 and 5). Each apple odorant included in the targeted water release groups by the inventors has an odor detection threshold of 50 ppb or less. These odor detection threshold values are also corroborated by the odor index values for these apple odorants. Based on these apple odorant's odor detection threshold values and odor indices as illustrated in the below examples, it is shown by the author that a strong apple note is present throughout the rinse-off experience when using this perfume.

TABLE 16

Apple Fragrance

| | parts | Ω |
|---|---|---|
| Water Release Group 1 | | |
| d-LIMONENE | 4.00 | 51.56 |
| ETHYL 2-METHYLBUTYRATE PURE FCC | 0.60 | 33.57 |
| total parts | 4.60 | |
| Water Release Group 2 | | |
| ETHYL BUTYRATE | 0.10 | 7.054 |
| METHYL PHENYL CARBINYL ACETATE | 1.20 | 1.19 |
| MANZANATE | 0.30 | 1.77 |
| HEXYL ACETATE | 0.80 | 1.16 |
| DIHYDROMYRCENOL | 5.00 | 0.32 |
| ALLYL CAPROATE | 0.40 | 0.15 |
| LINALOOL | 4.50 | 0.14 |

TABLE 16-continued

Apple Fragrance

| | parts | Ω |
|---|---|---|
| BENZYL ACETATE | 2.60 | 0.1 |
| TRICYCLODECENYL PROPIONATE | 1.00 | 0.08 |
| total parts Water Release Group 3 | 15.90 | |
| LINALYL ACETATE | 1.50 | 0.0598 |
| CIS-3-HEXENYL ACETATE | 0.30 | 0.0541 |
| CITRONELLOL AJ, FCC | 0.80 | 0.0463 |
| TRIPLAL | 0.20 | 0.0668 |
| VERDOX | 5.80 | 0.0564 |
| total parts Water Release Group 4 | 8.60 | |
| FRUCTONE | 0.15 | 0.00520 |
| LILIAL | 5.00 | 0.00298 |
| APHERMATE | 0.10 | 0.00331 |
| IONONE ALPHA REGULAR | 0.50 | 0.00314 |
| DIMETHYL BENZYL CARBINYL ACETATE | 0.60 | 0.00268 |
| ALLYL CYCLOHEXYL PROPIONATE | 1.00 | 0.00095 |
| FLOROL | 3.60 | 0.00068 |
| PHENOXY ETHYL ISOBUTYRATE | 6.00 | 0.00080 |
| total parts Water Release Group 5 | 16.95 | |
| ISO E SUPER | 5.50 | 0.000214 |
| DYNASCONE | 0.03 | 0.000266 |
| alpha-DAMASCONE | 0.10 | 0.000144 |
| GAMMA UNDECALACTONE | 0.30 | 0.000143 |
| GALAXOLIDE 50 IPM | 13.00 | 0.000037 |
| | 18.93 | |
| HELIONAL | 1.00 | 0.00002809 |
| HEDIONE | 19.00 | 0.00002169 |
| VERTOFIX COEUR | 1.50 | 0.00000679 |
| BACDANOL | 0.30 | 0.00000633 |
| BENZYL SALICYLATE | 12.35 | 0.00000146 |
| CIS-3-HEXENYL SALICYLATE | 0.50 | 0.00000013 |
| VANILLIN NF | 0.10 | 0.00000005 |
| total parts | 34.75 | |
| DIPROPYLENE GLYCOL | 17.22 | |
| TOTAL PERFUME PARTS | 100.00 | |

The odorants included in this particular perfume which contribute to the apple perfume are shown below in Table 17.

TABLE 17

| Apple Note Compounds | Γ (cm/sec$^2$) | ODT |
|---|---|---|
| ETHYL 2-METHYLBUTYRATE | 12827.56 | 50 ppb or less |
| MANZANATE | 5288.42 | 50 ppb or less |
| HEXYL ACETATE | 3118.78 | |
| VERDOX | 564.56 | |
| FRUCTONE | 554.79 | 50 ppb or less |
| APHERMATE | 589.62 | |
| Alpha-DAMASCONE | 157.30 | 50 ppb or less |

The authors will consider alpha-damascone as a contributor to the apple note although it is perceived alone as floral rose with some apple-blackcurrant plum undertones.

As mentioned above, the authors can also apply their odor index algorithm to gauge odor intensity of odorants and subsequently, predict the overall odor of each Water Release Group as well as the odor contribution of each apple odorant chosen in the Apple perfume. In the illustration below, the contribution to each of the apple odorants to the overall odor is estimated within each Water Release Groups containing the apple odorants, using odor impact equation [3] as shown earlier and rationale used in the Tropical Fruit Perfume in Table 18.

TABLE 18

| Water Release Group 1 | % Odor Contribution |
|---|---|
| d-LIMONENE | 26.09 |
| ETHYL 2-METHYLBUTYRATE | 73.91 |

Water Release Group 1 will therefore result in an apple-citrus odor upon immediate dilution. Both ethyl-2-methyl butyrate and d-limonene have "flash-release" Γ values, with ethyl-2-methyl butyrate giving a longer lasting perception due to its much lower odor detection threshold. The big difference in odor detection thresholds is also translated proportionally in the odorants' difference in odor indices.

The second "wave" of odorants eluting in Water Release Group 2, is almost 100% apple in its odor profile as shown below in Table 19.

TABLE 19

| Water Release Group 2 | % Odor Contribution |
|---|---|
| ETHYL BUTYRATE | 0.01 |
| METHYL PHENYL CARBINYL ACETATE | 0.01 |
| MANZANATE | 98.87 |
| HEXYL ACETATE | 0.01 |
| DIHYDROMYRCENOL | 0.10 |
| ALLYL CAPROATE | 0.02 |
| LINALOOL | 0.30 |
| BENZYL ACETATE | 0.03 |
| TRICYCLODECENYL PROPIONATE | 0.66 |

Manzanate's very large contribution to the overall odor of Water Release Group 2 is due to its very low odor detection threshold and odor index values in water, respectively 0.003 parts per billion and 0.001 parts per billion.

Water Release Group 3's apple comes mostly from verdox, a green apple odorant, thought to result in a long headspace residence time in rinse-off due to its Γ value of 564.56, characteristic of sustained release in water dilutions.

TABLE 20

| Water Release Group 3 | % Odor Contribution |
|---|---|
| LINALYL ACETATE | 1.64 |
| CIS-3-HEXENYL ACETATE | 8.18 |
| CITRONELLOL AJ, FCC | 12.12 |
| TRIPLAL | 7.79 |
| VERDOX | 51.55 |

Water Release Group 4 and 5 also have some apple character, which add to the overall background generated from the previously released odorants predicted to elute as shown above. The percentage contribution of the apple odorants to their overall character is shown below in Tables 21-22.

TABLE 21

| Water Release Group 4 | % Odor Contribution |
|---|---|
| FRUCTONE | 7.89 |
| LILIAL | 13.14 |
| APHERMATE | 0.20 |
| IONONE ALPHA REGULAR | 6.57 |

TABLE 21-continued

| Water Release Group 4 | % Odor Contribution |
|---|---|
| DIMETHYL BENZYL CARBINYL ACETATE | 0.40 |
| ALLYL CYCLOHEXYL PROPIONATE | 37.55 |
| FLOROL | 2.70 |
| PHENOXY ETHYL ISOBUTYRATE | 31.54 |

TABLE 22

| Water Release Group 5 | % Odor Contribution |
|---|---|
| ISO E SUPER | 28.24 |
| DYNASCONE | 0.02 |
| Alpha-DAMASCONE | 68.46 |
| GAMMA UNDECALACTONE | 0.62 |
| GALAXOLIDE 50 IPM | 2.67 |

No odorants contributing to the apple aspect of the perfume were found in Water Release Group 6.

The next perfume example is a "Floral" perfume designed to yield a sustained floral accord during rinse-off. It was constructed for linear release based on the criteria set forth by the authors in this invention.

Floral Fragrance

The following "Floral" fragrance is a perfume designed to give a long sustained linear release of a floral note from the beginning to the end of the rinse-off experience. The odorants are divided into Water Release Groups according to their water release values $\Omega$.

TABLE 23

| | parts | $\Omega$ |
|---|---|---|
| Water Release Group 1 | | |
| total parts | 0.00 | |
| Water Release Group 2 | | |
| MAYOL | 5.03 | 4.508429 |
| CYCLACET | 4.95 | 3.261580 |
| BENZYL ACETATE | 33.06 | 1.300902 |
| LINALOOL | 26.25 | 0.807717 |
| DIHYDROMYRCENOL | 5.6 | 0.355777 |
| LINALYL ACETATE | 8.19 | 0.326361 |
| CIS-3-HEXEN-1-OL | 1.04 | 0.266876 |
| TRIPLAL | 1.43 | 0.232993 |
| ROSE OXIDE (HIGH CIS) | 0.06 | 0.107096 |
| total parts | 85.61 | |
| Water Release Group 3 | | |
| CANTHOXAL | 0.57 | 0.029898 |
| IONONE BETA PURE | 3.6 | 0.026411 |
| LIFFAROME | 0.08 | 0.025139 |
| GALBANOLENE, SUPER | 0.12 | 0.023020 |
| NEOFOLIONE | 0.51 | 0.017724 |
| total parts | 4.88 | |
| Water Release Group 4 | | |
| ALPHA TERPINEOL | 0.59 | 0.002657 |
| FLORHYDRAL | 0.59 | 0.001145 |
| CIS 3 HEXENYL BENZOATE | 0.7 | 0.000559 |
| DIMETHYL PHENYL ETHYL CARBINOL | 0.13 | 0.000524 |
| MUGETANOL | 1.18 | 0.000518 |
| total parts | 3.19 | |
| Water Release Group 5 | | |
| BETA DAMASCONE FAB | 0.12 | 0.000210 |
| METHYL ANTHRANILATE REGULAR | 0.3 | 0.000100 |
| total parts | 0.42 | |

TABLE 23-continued

| | parts | $\Omega$ |
|---|---|---|
| Water Release Group 6 | | |
| HEDIONE | 5.9 | 0.000014 |
| total parts | 5.9 | |
| total perfume parts | 100 | |

Every odorant in the formula contributes to the floralcy of the released perfume. No odorants in the formula are found to elute in the defined "Water Release Group 1", or in other words have a water release value, $\Omega$ higher than 10. The release profile of the odorants along with their experimentally measured odor intensity is found below in Table 24.

TABLE 24

| | $\Gamma$ (cm/sec$^2$) | Odor Detection Threshold (ppb) |
|---|---|---|
| Water Release Group 2 | | |
| MAYOL | 2558.11201 | |
| CYCLACET | 1687.86800 | 50 ppb or less |
| BENZYL ACETATE | 664.28764 | |
| LINALOOL | 644.41282 | 50 ppb or less |
| DIHYDROMYRCENOL | 866.54502 | |
| LINALYL ACETATE | 617.71622 | |
| Water Release group 3 | | |
| CANTHOXAL | 684.36399 | |
| IONONE BETA PURE | 311.31669 | 50 ppb or less |
| LIFFAROME | 1515.53888 | |
| GALBANOLENE | 1501.13941 | |
| NEOFOLIONE | 653.99725 | |
| Water Release group 4 | | |
| ALPHA TERPINEOL | 269.84259 | |
| FLORHYDRAL | 180.11229 | 50 ppb or less |
| CIS 3 HEXENYL BENZOATE | 117.78151 | |
| DIMETHYL PHENYL ETHYL CARBINOL | 246.27049 | |
| MUGETANOL | 98.69552 | |
| Water Release group 5 | | |
| BETA DAMASCONE FAB | 171.98603 | 50 ppb or less |
| METHYL ANTHRANILATE REGULAR | 77.81181 | 50 ppb or less |
| Water Release group 6 | | |
| HEDIONE | | 50 ppb or less |

"Floral" perfume releases in rinse-off in typically linear fashion from beginning to end as it was constructed to do based on its mass transfer properties and rationale as defined in the herein invention. It is mostly composed of sustained release odorants (based on their $\Gamma$ values).

Bamboo and Cucumber Fragrance

The following perfume "Bamboo and Cucumber" was used as another illustrative example to engineer a sustained linear release for a specific note, in this particular care melon-cucumber during use in rinse-off conditions.

TABLE 25

| | PARTS | $\Omega$ |
|---|---|---|
| Water Release Group 1 | | |
| d-LIMONENE | 4.28 | 55.16971144 |
| ETHYL 2-METHYLBUTYRATE | 0.41 | 22.93862952 |

TABLE 25-continued

| | PARTS | Ω |
|---|---|---|
| Water Release Group 2 | | |
| ETHYL BUTYRATE | 0.09 | 6.34970816 |
| METHYL PHENYL CARBINYL ACETATE | 1.47 | 1.45429832 |
| HEXYL ACETATE | 0.35 | 0.50752370 |
| CYCLACET | 0.77 | 0.50735692 |
| DIHYDROMYRCENOL | 3.84 | 0.24396106 |
| ALLYL CAPROATE | 0.45 | 0.16472431 |
| BENZYL ACETATE | 3.33 | 0.13103463 |
| LINALYL ACETATE | 2.05 | 0.08168977 |
| CIS-3-HEXENYL ACETATE | 0.45 | 0.08110941 |
| Water Release Group 3 | | |
| VERDOX | 1.66 | 0.05868720 |
| CITRONELLOL | 0.96 | 0.05561816 |
| TRICYCLODECENYL PROPIONATE | 0.7 | 0.05378250 |
| MELONAL | 0.06 | 0.04937926 |
| TRIPLAL | 0.26 | 0.04236244 |
| METHYL PAMPLEMOUSSE | 0.29 | 0.01642029 |
| TETRAHYDROLINALOOL | 0.58 | 0.00973621 |
| LILIAL | 12.8 | 0.00762539 |
| PHENYL ETHYL ALCOHOL | 2.69 | 0.00735362 |
| Water Release Group 4 | | |
| BENZALDEHYDE | 0.03 | 0.00681827 |
| APHERMATE | 0.13 | 0.00429864 |
| 2,6-NONADIENAL | 0.03 | 0.00228471 |
| CYCLAMEN ALDEHYDE | 4.35 | 0.00206883 |
| PHENOXY ETHYL ISOBUTYRATE | 7.68 | 0.00102652 |
| ALLYL CYCLOHEXYL PROPIONATE | 1.02 | 0.00096498 |
| FLORHYDRAL | 0.45 | 0.00087340 |
| IONONE ALPHA | 0.13 | 0.00081751 |
| Water Release Group 5 | | |
| UNDECAVERTOL | 0.77 | 0.00040248 |
| 2,6 NONADIEN-1-OL | 0.04 | 0.00011885 |
| CIS JASMONE | 0.06 | 0.00010442 |
| DIMETHYL BENZYL CARBINYL BUTYRATE | 0.77 | 0.00005679 |
| HEDIONE | 22.47 | 0.00005397 |
| GALAXOLIDE 50 IPM | 17.28 | 0.00004982 |
| DAMASCENONE | 0.09 | 0.00004425 |
| DYNASCONE | 0.04 | 0.00003543 |
| Water Release Group 6 | | |
| HELIONAL | 0.7 | 0.00001966 |
| MAGNOLAN | 0.26 | 0.00001111 |
| GAMMA UNDECALACTONE | 0.13 | 0.00000845 |
| VERTOFIX | 1.6 | 0.00000724 |
| BACDANOL | 0.32 | 0.00000676 |
| DIHYDRO ISO JASMONATE | 0.38 | 0.00000052 |
| BENZYL SALICYLATE | 3.07 | 0.00000036 |
| MUSCONE | 0.06 | 0.00000013 |
| CIS-3-HEXENYL SALICYLATE | 0.51 | 0.00000013 |
| SINENSAL | 0.01 | 0.00000006 |
| VANILLIN NF | 0.13 | 0.00000006 |
| total perfume parts | 100 | |

The following odorants in Table 26 contribute to the cucumber-melon note.

TABLE 26

| | Γ (cm/sec$^2$) | ODT (ppb) |
|---|---|---|
| Water Release Group 3 | | |
| MELONAL | 2655.51866 | 50 ppb or less |
| Water Release Group 4 | | |
| 2,6-NONADIENAL | 1010.67236 | 50 ppb or less |
| Water Release Group 5 | | |
| 2,6-NONADIENOL | 245.87069 | 50 ppb or less |

This perfume gives a burst of a cucumber melon note between 10 and 20 seconds due to melonal, predicted to elute in Water Release Group 3. 2,6-Nonadienal from Water Release Group 4 contributes to the cucumber melon note, as a flash release odorant as well. Both of these odorants have low odor detection threshold values in water: 16 ppb and 0.01 ppb for melonal and 2,6-nonadienal respectively. Once released in air, due to its very low odor detection threshold value, 2,6-nonadienal will have a very large impact on the overall perfume released from the dilution partitions. 2,6-Nonadienol will bring about a very sustained release based on its Γ value and relatively low odor detection threshold value in water: 1 part per billion.

Delayed Release of Fragrance Notes

In other instances, the action of the delivered benefit agent is emphasized by a delayed release of the accompanying hedonic note during wash-off. The consumer will be able to experience a sensory perception of the conditioning or beneficial extract included in the product upon subsequent physical contact with water.

By engineering the fragrance to include a hedonic note that is released much later that many of the odorants during the wash-off experience, one can give the impression of a delayed release of the particular wanted odor or fragrance note. For example, by including a fragrance note in the latter water release groups i.e. water release groups 3, 4 and 5 and more preferably release group 4 and/or 5 and/or 6 based on water release values defined in the invention and by not including the desired targeted olfactive note in the earlier water release groups, one can bring about a sudden change in the fragrance without the inclusion of any additional delivery vehicles such as encapsulation and/or other polymeric vehicles.

It is also preferable that the desired olfactive note is given by a single odorant and/or a combination of odorants within the latter water release groups (subsequent to Water Release Group 3) and that at least one odorant that results in the desired odor has an odor detection threshold in water or a water odor index of less than 50 parts per billion and/or an air odor detection threshold and/or an air odor index of less than 0.025 mg/m$^3$.

As an illustrative example, a perfume with a delayed fig note is shown below.

TABLE 27

"Citrus Floral" Perfume

| | | parts | Ω. |
|---|---|---|---|
| Group 1 | ORANGE TERPENES | 7.17 | 92.42 |
| | LEMON OIL DISTILLED NATURAL | 5.74 | 73.99 |
| Group 2 | ETHYL 2-METHYLBUTYRATE PURE FCC | 0.10 | 5.59 |
| | ETHYL BUTYRATE | 0.11 | 7.76 |
| | HEXYL ACETATE | 0.35 | 0.51 |
| | DIHYDROMYRCENOL | 4.41 | 0.28 |
| | LINALOOL | 8.83 | 0.27 |
| Group 3 | TRIPLAL | 0.20 | 0.067 |
| | CIS-3-HEXENYL ACETATE | 0.30 | 0.054 |
| | CITRONELLYL NITRILE | 0.64 | 0.031 |
| Group 4 | PHENOXY ETHYL ISOBUTYRATE | 20.00 | 0.0027 |
| | GAMMA UNDECALACTONE | 1.10 | 0.00052 |
| | PYROPRUNAT | 10.00 | 0.00054 |
| | δ-DAMASCONE | 0.30 | 0.00050 |
| Group 5 | DIMETHYL BENZYL CARBINYL BUTYRATE | 4.41 | 0.000325 |
| | METHYL ANTHRANILATE REGULAR | 0.44 | 0.000100 |
| | HELIONAL | 2.21 | 0.000062 |

TABLE 27-continued

"Citrus Floral" Perfume

| | | parts | Ω. |
|---|---|---|---|
| Group 6 | HEDIONE | 11.04 | 0.000013 |
| | NECTARYL | 0.44 | 0.0000031 |
| | BENZYL SALICYLATE | 21.77 | 0.0000026 |
| | ETHYL VANILLIN | 0.44 | 0.0000005 |

The fig note is given by pyroprunat, δ-damascone and dimethyl benzyl carbinyl butyrate and their properties are shown below in Table 28.

TABLE 28

| | Γ (cm/sec$^2$) | ODT (ppb) |
|---|---|---|
| Water Release Group 4 | | |
| PYROPRUNAT | 34.08 | |
| δ-DAMASCONE | 162.39 | 50 ppb or less |
| Water Release Group 5 | | |
| DIMETHYL BENZYL CARBINYL BUTYRATE | 39.87 | |

When put at a regular concentration in a rinse-off product, the perfume will release a progressively citrus floral (1 to 30 seconds upon water contact) in high dilutions of water. Subsequently, a dry fig note will appear later on during the wash-off experience: 30-40 seconds upon dilution. The release of the fig note will be very gradual rather sudden, based on the relatively low Γ values for the odorants involved giving the perception of a fig note (see above values)

The following perfume example: "Water Blossoms" is engineered to give off a delayed berry note once diluted in water based on the chosen odorants' water release values Ω.

TABLE 29

"Water Blossoms" Fragrance

| | parts | Ω |
|---|---|---|
| Water Release Group 1 | | |
| D-LIMONENE | 9.55 | 98.60941413 |
| Water Release Group 2 | | |
| MAYOL | 3.00 | 2.6847 |
| CYCLACET | 2.96 | 1.9486 |
| BENZYL ACETATE | 23.70 | 0.9325 |
| LINALOOL | 18.96 | 0.5833 |
| LINALYL ACETATE | 4.90 | 0.1953 |
| CIS-3-HEXEN-1-OL | 0.62 | 0.1581 |
| TRIPLAL | 0.84 | 0.1374 |
| DIHYDROMYRCENOL | 1.90 | 0.1204 |
| Water Release Group 3 | | |
| ROSE OXIDE (HIGH CIS) | 0.04 | 0.06765 |
| TETRAHYDROLINALOOL | 2.54 | 0.04264 |
| CIS-3-HEXENYL ACETATE | 0.21 | 0.03758 |
| CANTHOXAL | 0.35 | 0.01840 |
| NEOFOLIONE | 0.30 | 0.01054 |
| ETHYL LINALOOL | 1.90 | 0.00794 |
| Water Release Group 4 | | |
| ALPHA TERPINEOL | 0.32 | 0.00145 |
| FLORHYDRAL | 0.35 | 0.00068 |
| Water Release group 5 | | |
| BETA DAMASCONE FAB | 0.20 | 0.000349 |
| CIS 3 HEXENYL BENZOATE | 0.43 | 0.000340 |

TABLE 29-continued

"Water Blossoms" Fragrance

| | parts | Ω |
|---|---|---|
| MUGETANOL | 0.71 | 0.000312 |
| DIMETHYL PHENYL ETHYL CARBINOL | 0.08 | 0.000306 |
| cis-JASMONE | 0.09 | 0.000165 |
| METHOXY PHENYL BUTANONE | 2.02 | 0.000137 |
| ISO E SUPER | 1.90 | 0.000074 |
| ETHYL PHENYL GLYCIDATE | 2.02 | 0.000062 |
| Water Release Group 6 | | |
| DAMASCENONE | 0.06 | 0.00002798 |
| OXANONE CRYSTALS | 4.27 | 0.00001114 |
| HEDIONE | 3.52 | 0.00000845 |
| HABANOLIDE | 1.90 | 0.00000624 |
| BENZYL SALICYLATE | 9.48 | 0.00000112 |
| STRAWBERRY FURANONE | 0.01 | 0.00000002 |
| PHENYL ETHYL SALICYLATE | 0.91 | 0.000000002 |
| PERFUME TOTAL | 100.00 | |

The fragrance odorants which will contribute to the delayed berry note appear in Water Release Groups 5 and 6 and are as follow in Table 30.

TABLE 30

| Odorant | Γ (cm/sec$^2$) | ODT (ppb) |
|---|---|---|
| β-damascone | 171.97 | 50 ppb or less |
| Methoxyphenyl Butanone | 41.25 | |
| Ethyl Phenyl Glycidate | 26.35 | 50 ppb or less |
| Oxanone | 41.24 | 50 ppb or less |
| Strawberry Furanone | 2.49 | 50 ppb or less |

The Water Blossoms" fragrance gave an initial floral fragrance when first used in rinse-off and then a change into a berry odor after around 30 seconds from the time of dilution. The appearance of the berry note is also gradual based on the Γ values of odorants chosen.

The following perfume "Zesty White Floral" illustrates the use of water release values Ω and overall mass transfer properties of odorants (Γ and φ), while taking in consideration their concentrations within the overall perfume formula to construct the delayed release of an odor note. The delayed note in this particular example is sudden rather than gradual since the Γ values used for the odorants in the delayed fragrance note are relatively high.

TABLE 31

"Zesty White" Floral

| | parts | Ω |
|---|---|---|
| Water Release Group 1 | | |
| total parts | 0 | |
| Water Release Group 2 | | |
| CYCLACET | 4.20 | 2.7674014 |
| BENZYL ACETATE | 11.50 | 0.4525220 |
| LINALOOL | 12.36 | 0.3803192 |
| CITRONELLOL | 2.47 | 0.1431009 |
| total parts | 30.53 | |
| Water Release Group 3 | | |
| METHYL IONONE GAMMA A | 3.09 | 0.0498085 |
| total parts | 3.09 | |

TABLE 31-continued

"Zesty White" Floral

| | parts | Ω |
|---|---|---|
| Water Release Group 4 | | |
| FLORALOZONE | 3.71 | 0.0057567 |
| METHYL IONONE ALPHA EXTRA | 0.99 | 0.0047213 |
| CITRONELLYL ACETATE | 0.37 | 0.0044622 |
| ALDEHYDE C-18 | 0.37 | 0.0017855 |
| PHENYL ETHYL ALCOHOL | 4.02 | 0.0015668 |
| ALLYL AMYL GLYCOLATE | 0.90 | 0.0015343 |
| GERANIOL | 0.59 | 0.0014488 |
| LILIAL | 1.98 | 0.0011796 |
| total parts | 12.93 | |
| Water Release Group 5 | | |
| HEXYL CINNAMIC ALDEHYDE | 29.67 | 0.0004837 |
| JASMAL | 0.84 | 0.0004816 |
| METHYL ANTHRANILATE REGULAR | 0.72 | 0.0001646 |
| GAMMA UNDECALACTONE | 1.48 | 0.0000962 |
| METHYL ISO EUGENOL | 1.09 | 0.0000790 |
| TRANS-4-DECEN-1-AL (0.1% Solution in Dipropylene Glycol) | 0.49 | 0.0000477 |
| total parts | 34.29 | |
| Water Release Group 6 | | |
| EUGENOL | 0.15 | 0.0000261 |
| 1-p-MENTHENE-8-THIOL 1% Solution in Alc. (10% IN DIPROPYLENE GLYCOL) | 0.12 | 0.0000129 |
| THIOGERANIOL (0.05% IN DIPROPYLENE GLYCOL) | 0.10 | 0.0000015 |
| AMYL SALICYLATE | 1.36 | 0.0000005 |
| MANDARIN ALDEHYDE (0.1% IN DIPROPYLENE GLYCOL) | 0.49 | 0.0000002 |
| ATRALONE | 0.87 | 0.000000003 |
| total parts | 83.93 | |
| DIPROPYLENE GLYCOL | 16.07 | |
| total perfume parts | 100 | |

The following odorants in the perfume contribute to the citrus note, as shown in Table 32.

TABLE 32

| | Γ (cm/sec²) | ODT (ppb) |
|---|---|---|
| Water Release Group 5 | | |
| TRANS-4-DECEN-1-AL | 1076.65 | 50 ppb or less |
| Water Release Group 6 | | |
| MANDARIN ALDEHYDE | 90.29 | 50 ppb or less |
| THIOGERANIOL | 659.09 | 50 ppb or less |
| 1-p-MENTHENE-8-THIOL | 1043.22 | 50 ppb or less |

The Γ values for trans-4-decenal and 1-p-menthene-8-thiol are indicative of flash release and thiogeraniol will give more of a sustained release once diluted in rinse-off conditions. These properties will give the perception of a delayed citrus burst as opposed to a gradual burst as discussed in the previous examples. It is also important to note that trans-4-decenal; thiogeraniol and 1-p-menthene-8-thiol are classically considered "top notes" and were thought to be blooming odorants according to the prior art. Their boiling point and clogP values are shown in Table 33.

TABLE 33

| | clogP | Boiling Point deg C. |
|---|---|---|
| Water Release Group 5 | | |
| TRANS-4-DECEN-1-AL | 3.77 | 200 |
| Water Release Group 6 | | |
| THIOGERANIOL | 4.88 | 250 |
| 1-p-MENTHENE-8-THIOL | 4.74 | 229 |

The above description is for the purposes of teaching the person of ordinary skill in the art how to practice the present invention, and it is not intended to detail all those obvious modifications and variations of it which will become apparent to the skilled worker upon reading the description.

What is claimed is:

1. A method of formulating a perfume composition for rinse-off or high dilution systems, comprising:
   calculating water release (Ω) values for a group of odorants;
   selecting at least three odorants eluting from different water release, Ω, value ranges selected from the group consisting of range 1, Ω value from and including 10 and greater, range 2, Ω value from and including 0.07 to 10, range 3, Ω value from and including 0.007 and to 0.07, range 4, Ω value from and including 0.0005 to 0.007, range 5, Ω value from and including 0.00003 to 0.0005, and range 6, Ω value of less than 0.00003 including the selected odorants in the perfume composition for a rinse-off or high dilution system to provide a linear release of a perfume note during use.

2. The method of claim 1, further comprising the step of selecting at least one odorant eluting from water release value range selected from the group consisting of range 1, range 2, and range 3.

3. The method of claim 1, further comprising the steps of:
   calculating acceleration (Γ) values for a group of odorants; and
   selecting at least one odorant having an acceleration (Γ) value of from about 100 to about 1000 cm/sec².

4. The method of claim 1, further comprising the steps of:
   calculating values of odor detection threshold in water, odor detection threshold in air, odor index in water, and odor index in air for a group of odorants; and
   selecting at least one odorant having a value selected from the group consisting of an odor detection threshold in water of about 50 parts per billion or less, an odor index value in water of about 50 parts per billion or less, an odor detection threshold in air of about 0.025 mg/m³ or less, and an odor index in air of about 0.025 mg/m³ or less, and combinations of these.

5. The method of claim 1, wherein the selected odorants comprise at least about 30% of the perfume composition.

6. The method of claim 1, wherein the selected odorants comprise at least about 40% of the perfume composition.

7. A method of formulating a perfume composition for rinse-off or high dilution systems, comprising:
   calculating values of water release (Ω), acceleration (Γ), odor detection threshold in water, odor detection threshold in air, odor index in water, and odor index in air for a group of odorants;
   selecting at least three odorants eluting from different water release (Ω) value ranges selected from the group consisting of range 1, Ω value from and including 10 and greater, range 2, Ω value from and including 0.07 to 10, range 3, Ω value from and including 0.007 and to 0.07, range 4, Ω value from and including 0.0005 to 0.007, range 5, Ω value from and including 0.00003 to 0.0005, and range 6, Ω value of less than 0.00003, wherein at least one of the selected odorants elutes from either range 1, range 2, or range 3;

selecting at least on odorant having an acceleration (Γ) value of from about 100 to about 1000 cm/sec2, selecting at least one odorant having a property selected from the group consisting of an odor detection threshold in water of about 50 parts per billion or less, an odor index value in water of about 50 parts per billion or less, an odor detection threshold in air of about 0.025 mg/m3 or less, and an odor index in air of about 0.025 mg/m3 or less, and combinations of these; and including the selected odorants in the perfume composition to provide a linear release of a perfume note during use of the system, wherein the selected odorants comprise a least about 30% of the perfume composition.

8. The method of claim 7, wherein the selected odorants comprise at least about 40% of the perfume composition.

9. A method of formulating a perfume composition for rinse-off or high dilution systems, comprising:

calculating water release (Ω) values for a group of odorants;

selecting at least two odorants eluting from water release (Ω) value ranges selected from the group consisting of range 4, Ω value from and including 0.0005 to 0.007, range 5, Ω value from and including 0.00003 to 0.0005, and range 6, Ω value of less than 0.00003; and placing the selected odorants in the perfume composition for a rinse-off or high dilution system to provide a delayed release of a perfume note during use.

10. The method of claim 9, comprising selecting at least three odorants eluting from water release (Ω) value ranges selected from the group consisting of range 4, range 5 and range 6.

11. The method of claim 9, comprising selecting at least two odorants eluting from water release (Ω) value ranges selected from the group consisting of range 5 and range 6.

12. The method of claim 9, further comprising the steps of:
calculating acceleration (Γ) values for a group of odorants; and
selecting at least one odorant having an acceleration (Γ) value of from about 100 to about 1000 cm/sec$^2$.

13. The method of claim 9, further comprising the steps of:
calculating values of odor detection threshold in water, odor detection threshold in air, odor index in water, and odor index in air for a group of odorants; and selecting at least one odorant having a property selected from the group consisting of an odor detection threshold in water of about 50 parts per billion or less, an odor index value in water of about 50 parts per billion or less, an odor detection threshold in air of about 0.025 mg/m$^3$ or less, and an odor index in air of about 0.025 mg/m$^3$ or less, and combinations of these.

14. The method of claim 9, wherein the selected odorants comprise at least about 30% of the perfume composition.

15. A method of claim 9, wherein the odorants comprise at least about 40% of the perfume composition.

16. A method of formulating a perfume composition for rinse-off or high dilution systems, comprising:

calculating values of water release (Ω), acceleration (Γ), odor detection threshold in water, odor detection threshold in air, odor index in water, and odor index in air for a group of odorants;

selecting at least two odorants eluting from different water release (Ω) value ranges selected from the group consisting of range 4, Ω value from and including 0.0005 to 0.007, range 5, Ω value from and including 0.00003 to 0.0005, and range 6, Ω value of less than 0.00003;

selecting at least on odorant having an acceleration (Γ) value of from about 100 to about 1000 cm/sec$^2$, selecting at least one odorant having a property selected from the group consisting of an odor detection threshold in water of about 50 parts per billion or less, an odor index value in water of about 50 parts per billion or less, an odor detection threshold in air of about 0.025 mg/m3 or less, and an odor index in air of about 0.025 mg/m$^3$ or less, and combinations of these; and combining the selected odorants to comprise at least about 30% of the perfume composition to provide a delayed release of a perfume note during use of the system.

17. The method of claim 16, comprising selecting at least three odorants eluting from water release (Ω) value ranges selected from the group consisting of range 4, range 5 and range 6.

18. The method of claim 16, comprising selecting at least two odorants eluting from water release (Ω) value ranges selected from the group consisting of range 5 and range 6.

19. The method of claim 16, wherein the selected odorants comprise at least about 40% of the perfume composition.

20. The method of claim 16, comprising selecting at least three odorants eluting from water release (Ω) value ranges selected from the group consisting of range 5 and range 6.

* * * * *